US006872385B2

(12) United States Patent
Fidler et al.

(10) Patent No.: US 6,872,385 B2
(45) Date of Patent: Mar. 29, 2005

(54) ADJUVANT PREPARATION FOR THE INDUCTION OF SPECIFIC IMMUNITY

(75) Inventors: Isaiah J. Fidler, Houston, TX (US); Zhongyun Dong, Sugar Land, TX (US); Weixin Lu, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 12 days.

(21) Appl. No.: 09/872,162

(22) Filed: May 31, 2001

(65) Prior Publication Data

US 2003/0206890 A1 Nov. 6, 2003

Related U.S. Application Data

(60) Provisional application No. 60/208,436, filed on May 31, 2000.

(51) Int. Cl.[7] .................. A61K 38/21; A61K 48/00; A61K 45/00; A01N 63/00; C12N 15/63
(52) U.S. Cl. ............... 424/85.6; 424/93.21; 424/93.3; 424/278.1; 435/320.1; 435/455
(58) Field of Search ................ 424/85.6, 93.21, 424/93.3, 278.1, 279.1; 435/320.1, 455

(56) References Cited

U.S. PATENT DOCUMENTS

| | | | |
|---|---|---|---|
| 4,215,051 A | 7/1980 | Schroeder et al. | 260/346.7 |
| 4,745,051 A | 5/1988 | Smith et al. | 435/68 |
| 4,879,236 A | 11/1989 | Smith et al. | 435/235 |
| 5,077,214 A | 12/1991 | Guarino et al. | 435/240.2 |
| 5,098,702 A | 3/1992 | Zimmerman et al. | 424/85.21 |
| 5,155,037 A | 10/1992 | Summers | 435/240.2 |
| 5,162,222 A | 11/1992 | Guarino et al. | 435/240.2 |
| 5,169,784 A | 12/1992 | Summers et al. | 435/320.1 |
| 5,278,050 A | 1/1994 | Summers | 435/69.1 |
| 5,498,540 A | 3/1996 | Sawyer et al. | 435/240.2 |
| 5,681,562 A * | 10/1997 | Sobol et al. | 424/93.21 |
| 5,759,809 A | 6/1998 | Iatrou | 435/69.1 |
| 6,224,882 B1 * | 5/2001 | Smith et al. | 424/279.1 |

FOREIGN PATENT DOCUMENTS

| | | |
|---|---|---|
| WO | WO 89/01038 | 2/1989 |
| WO | WO 93/07906 | 4/1993 |
| WO | WO 98/25574 | 6/1998 |
| WO | WO 99/24049 | 5/1999 |
| WO | WO 00/20561 | 4/2000 |
| WO | WO 00/55345 | 9/2001 |

OTHER PUBLICATIONS

Ayres et al., "The Complete DNA Sequence of *Autographa californica* Nuclear Polyhedrosis Virus," *Virology* 202:586–605, 1994.
Bernards, et al., "Effective Tumor Immunotherapy Directed Against An Oncogene–Encoded Product Using A Vaccinia Virgus Vector," *Proc. Nat'l Acad. Sci. USA*, 84:6854–6858, 1987.
Blissard and Rohrmann, "Location, Sequence, Transcriptional Mapping, and Temporal Expression of the gp64 Envelope Glycoprotein Gene of the *Orgyia pseudotsugata* Multicapsid Nuclear Polyhedrosis Virus," Virology 170:537–555, 1989.
Blissard and Rohrmann, "Baculovirus Diversity and Molecular Biology," *Annu. Rev. Entomol.* 35:127–155, 1990.
Carson et al., "Functional Mapping of an AcNPV Immediately Early Gene Which Augments Expression of the IE–1trans–Activated 39K Gene," *Virology*, 162:444–451, 1988.
Carson et al., "Transient Expression of the *Autographa californica* Nuclear Polyhedrosis Virus Immediate–Early Gene, IE–N, Is Regulated by Three Viral Elements," *J. Virol.*, 65:945–951, 1991.
Charlton and Volkman, "Penetration of *Autographa californica* Nuclear Polyhedrosis Virus Nucleocapsids into IPLB Sf 21 Cells Induces Actin Cable Formation," Virology, 197, 245–254, 1993.
DeGiovanni et al., Immunological and Non–Immunological Influence of H–2K$^b$ Gene Transfection On The Metastatic Ability of B16 Melanoma Cells, *Int. J. Cancer*, 48:270–276, 1991.
Dinney et al., "Inhibition of Basic Fibroblast Growth Factor Expression, Angiogensis, and Growth of Human Bladder Carcinoma in Mice by Systemic Interferon–α Administration," *Cancer Res.,* 58: 808–814, 1998.
Dong et al., "Suppression Of Tumorigenicity And Metastasis In Murine UV–2237 Fibrosarcoma Cells By Infection With A Retroviral Vector Harboring The Interferon–Beta Gene," *Cancer Immuno. Immunother.,* 46: 137–146, 1998.
Dong et al., "Suppression of Angiogenesis, Tumorigenicity, and Metastasis by Human Prostate Cancer Cells Engineered to Produce Interferon–β," *Cancer Res.,* 59: 872–879, 1999.
Dranoff et al., "Vaccination With Irradiated Tumor Cells Engineered To Secrete Murine Granulocyte–Macrophage Colony–Stimulating Factor Stimulates Potent, Specific, And Long–Lasting Anti–Tumor Immunity," *Proc. Nat'l Acad. Sci. USA,* 90:3539–3543, 1993.

(Continued)

Primary Examiner—David Guzo
Assistant Examiner—Quang Nguyen
(74) Attorney, Agent, or Firm—Fulbright & Jaworski

(57) ABSTRACT

Disclosed are methods and compositions useful in the recruitment, activation and initiation of proliferation of immune cells. The instant invention relates to the discovery that specific insect cells and insect cell compositions exhibit adjuvant properties. The added benefit of this system is that the insect cells utilized may be transformed with an expression system and thus proteins may be introduced into the composition through direct protein expression by the cells. The claimed compositions and methods are particularly relevant in anti-tumor and cancer therapy. Of specific interest is the ability of the compositions of the invention to elicit a response that controls not only the primary tumor but also any metastatic cells or metastatic tumors which subsequently arise.

6 Claims, 24 Drawing Sheets

OTHER PUBLICATIONS

Einhorn and Grander, "Why do so many cancer patients fail to respond to interferon therapy?" *J. Interferon and Cytokine Res.*, 16:275–281, 1996.

Elliott et al., "Perspectives on the Role of MHC Antigens in Normal and Malignant Cell Development," *Adv. Cancer Res.*, 53:181–245, 1989.

Estin et al., "Recombinant Vaccinia Virus Vaccine Against The Human Melanoma Antigen P97 For Use In Immunotherapy," *Proc. Nat'l Acad. Sci. USA*, 85: 1052–1056, 1988.

Fabra et al., "Modulation Of The Invasive Phenotype Of Human Colon Carcinoma Cells By Organ Specific Fibroblasts Of Nude Mice," *Differentiation*, 52: 101–110, 1992.

Fidler, "Critical determinants of cancer metastasis: rationale for therapy," *Cancer Chemother. Pharmacol.*, 43 suppl:S3–S10, 1999.

Flannery and Sandy, "Aggrecan catabolism in cartilage: Studies on the nature of a novel proteinase (aggrecanase) which cleaves the Glu373–Ala374 bond of the interglobular domain," $39^{th}$ Annulal Meeting of Orthopaedic Research Society, p. 190, 1993.

Gariglio et al., "Therapeutic uterine–cervix cancer vaccines in humans," *Arch. Med. Res.*, 29:279–284, 1998.

Gohji et al., "Regulation of Gelatinase Production in Metastatic Renal Cell Carcinoma by Organ–specific Fibroblasts," *Jpn. J. Cancer Res.*, 85: 152–160, 1994a.

Gohji et al., "Human Recombinant Interferons–Beta and – Gamma Decrease Gelatinase Production and Invasion by Human KG–2 Renal–Carcinoma Cells," *Int. J. Cancer*, 58: 380–384, 1994b.

Groner, "Specificity and Safety of Baculoviruses," In: *The Biology of Baculoviruses*, R.R. Granados and B.A. Federici (Eds.), CRC Press, Boca Raton, FL., pp. 177–202, 1986.

Guarino and Smith, "Nucleotide Sequence and Characterization of the 39K Gene Region of *Autographa californica* Nuclear Polyhedrosis Virus," *Virology*, 179:1–8, 1990.

Guarino and Summers, "Nucleotide Sequence and Temporal Expression of a Baculovirus Regulatory Gene," *J. Virol.*, 61:2091–2099, 1987.

Guarino et al., "Complete Sequence and Enhancer Function of the Homologous DNA Regions of *Autographa californica* Nuclear Polyhedrosis Virus," *J. Virol.*, 60:224–229, 1986.

Guarino et al., "Ubiquitin Is Attached to Membranes of Baculovirus Particles by a Novel Type of Phospholipid Anchor," *Cell*, 80:301–309, 1995.

Hooft van Iddekinge et al., "Nucleotide Sequence of the Polyhedrin Gene of *Autographa californica* Nuclear Polyhedrosis Virus," *Virology*, 131:561–565, 1983.

Hu et al., "Characterization of a Recombinant Vaccinia Virus Expressing Human Melanoma–Associated Antigen p97," *J. Virol.*, 62: 176–180, 1988.

Kaufman et al., "A Recombinant Vaccinia Virus Expressing Human Carcinoembryonic Antigen (CEA)," *Int. J. Cancer*, 48:900–907, 1991.

Kim and Cohen., "MHC Antigen Expression by Melanomas Recovered from Mice treated with Allogeneic Mouse Fibroblasts Genetically Modified for Interleukin–2 Secretion and the Expression of Melanoma–Associated Antigens," *Cancer Immunol. Immunother.*, 38:185–193, 1994.

Kozuma and Hakuhara, "Fusion Characteristics of a Nuclear Polyhedrosis Virus in Cultured Cells: Time Course and Effect of a Synergistic Factor and pH," *J. Invert. Pathol.*, 63:63–67, 1994.

Kuzio et al., "Nucleotide Sequence of the p10 Polypeptide Gene of *Autographa californica* Nuclear Polyhedrosis Virus," *Virology*, 139:414–418, 1984.

Lu et al., "Eradication of primary tumors and induction of systemic immunity by an intralesional injection of baculovirus system–mediated interferon–beta gene therapy," Abstract, *Proc. Amer. Assoc. Cancer Res. Ann. Meeting*, 41:470, 2000.

Lu et al., "Insect cells transduced with a baculoviral vector encoding murine interferon–β as a novel therapeutic cancer vaccine," Abstract, *UT MD Anderson Cancer Center, Houston, TX*.

Martignoni et al., "Baculovirus of *Autographa californica* (*Lepidoptera: noctuidae*): a Candidate Biological Control Agent for Douglas–Fir Tussock Moth (*Lepidoptera: lymantriidae*)," *J. Econ. Entomol.*, 75:1120–1124, 1982.

McCluskie et al., "Route and method of delivery of DNA vaccine influence immune responses in mice and non–human primates," *Mol. Med.*, 5:287–300, 1999.

McCown et al., "Protection of mice against lethal Japanese encephalitis with a recombinant baculovirus vaccine," *Am. J. Trop. Med. Hyg.*, 42(5):491–499, 1990.

Pardoll, et al., "New Strategies for Active Immunotherapy with Genetically Engineered Tumor Cells," *Curr. Opin. Immunol.*, 4:619–623, 1992.

Pardoll, "Cancer Vaccines," *Immunol. Today*, 14:310–316, 1993.

Porgador et al., "H–$2K^b$ Transfection of B16 Melanoma Cells Results in Reduced Tumourigenicity and Metastic Competence," *J. Immunogenet.*, 16:291–303, 1989.

Porgador, et al., "Antimetastatic Vaccination of Tumor–Bearing Mice with Two Types of IFN-$_\gamma$ Gene–Inserted Tumor Cells," *J. Immunol.*, 150:1458–1470, 1993b.

Rosenberg et al., "The Immunotherapy and Gene Therapy of Cancer," *Clin. Oncol.*, 10:180–199, 1992.

Ruby et al., "Recombinant Virus Vectors That Coexpress Cytokines—A New Vaccine Strategy," *Vaccine Res.*, 1:347–356, 1992.

Sibille et al., "Structure of the Gene of tum—Transplantation Antigen P198: A Point Mutation Generates a New Antigenic Peptide," *J. Ex. Med.*, 172:35–45, 1990.

Singh et al., "Interferons α and β Down–Regulate the Expression of Basic Fibroblast Growth Factor in Human Carcinomas," *Proc. Nat'l Acad. Sci USA*, 92: 4562–4566, 1995.

Singh et al., "Cell Density–Dependent Modulation of Basic Fibroblast Growth Factor Expression by Human Interferon–β," *Int. J. Oncol.*, 8:649–656, 1996a.

Singh et al., "Interferon–β Prevents the Upregulation of Interleukin–8 Expression in Human Melanoma Cells," *J. Interferon Cytokine Res.*, 16:577–584, 1996b.

Singh and Fidler, "Systemic Administration of Interferons for Inhibition of Cancer Metastasis,"In: *Clinical Application of Interferons*, (ed. Stuart–Harris and Penney), pp. 391–405, Chapman & Hall, London, 1997.

Smith and Blobel, "The First Membrane Spanning Region of the Lamin B Receptor Is Sufficient for Sorting to the Inner Nuclear Membrane," *J. Cell. Biol.*, 120:631–637, 1993.

Stokes et al., "High level expression of equine herpesvirus 1 glycoproteins D and H and their role in protection against virus challenge in the C3H (H–2K) murine model," *Viris Res.*, 50:159–173, 1997.

Stokes et al., "The expression of the proteins of equine herpesvirus 1 which share homology with herpes simplex virus 1 glycoproteins H and L," *Virus Res.,* 40:91–107, 1996.

Tanaka et al., "Role of the Major Histocompatibility Complex Class I Antigens in Tumor Growth and Metastasis," *Ann. Rev. Immunol.,* 6:359–380, 1988.

Thiem and Miller, "Identification, Sequence, and Transcriptional Mapping of the Major Capsid Protein Gene of the Baculovirus *Autographa californica* Nuclear Polyhedrosis Virus," *J. Virol.,* 63:2008–2018, 1989.

Volkman, "The 64K Envelope Protein of Budded *Autographa californica* Nuclear Polyhedrosis Virus," *Curr. Top. Microbiol. Immunol.,* 131:103–118, 1986.

Volkman et al., "Alternate Pathway of Entry of Budded *Autographa californica* Nuclear Polyhedrosis Virus: Fusion at the Plasma Membrane," Virology, 148:288–297, 1986.

Whitford and Faulkner, "A Structural Polypeptide of the Baculovirus *Autographa californica* Nuclear Polyhedrosis Virus Contains O–Linked N–Acetylglucosamine," *J. Virol.,* 66:3324–3329, 1992a.

Whitford and Faulkner, "Nucleotide Sequence and Transcriptional Analysis of Gene Encoding gy41, a Structural Glycoprotein of the Baculovirus *Autographa californica* Nuclear Polyhedrosis Virus," *J. Virol.,* 66:4763–4768. [Authors' correction (1993) *J. Virol.,* 67:2427], 1992b.

Whitford et al., "Identification and Sequence Analysis of a Gene Encoding gp67, an Abundant Envelope Glycoprotein of the Baculovirus *Autographa californica* Nuclear Polyhedrosis Virus," *J. Virol.,* 63:1393–1399, 1989.

Xie et al., "Abrogation of Tumorigenicity and Metastasis of Murine and Human Tumor Cells by Transfection with the Murine IFN–β Gene: Possible Role of Nitric Oxide," *Clin. Cancer Res.* 3:2283–2294, 1997.

Naftzger et al., "Immune response to a different antigen induced by altered antigen: a study of tumor rejection and autoimmunity," *Proc. Natl. Acad. Sci., USA,* 93:14809–14814, 1996.

Sun et al., "DNA as an adjuvant: capacity of insect DAN and synthetic oligodeoxynucloetides to augment T cell responses to specific antigen," *J. Exp. Med.,* 187:1145–1150, 1998.

* cited by examiner

FIG. 13

| Tumors | Treatment of Subcutaneous Tumors | | Lung Metastasis Median (Range) | |
|---|---|---|---|---|
| | Treatment | Results | UV2237m | K1735 |
| UV2237m | Saline | Progression | 44(8-79) | >200(140->200) |
| UV2237m | H5IFNb | Regression | 0(All)* | >200(5->200) |
| K1735 | Saline | Progression | 120(74-178) | 92(44-152) |
| K1735 | H5IFNb | Regression | 121(14-131) | 0(All)* |

*P<0.001, N=5, one of two representative experiments is shown.

UV2237m or K1735m2 cells were inoculated s.c. into C3H/HeN mice, when tumors were 4 mm in diameter, the mice were injected i.v. with either UV2237m or K1735m2 cells, 2 days later, the s.c. tumors were injected with saline or lyophilized H5IFNβ(2×10⁶ cells-equivalent) (one injection for UV2237, 2 injections at 1wk interval for K1735m2). The diameter of s.c. tumors was determined every 5 days. The mice were killed and the number of lung metastases was counted 28 days after i.v. injection of the tumor cells.

Induction of specific tumor immunity in C3H mice cured of UV2237m or K1735m2 primary subcutaneous tumors

| Group | s.c. Challenge Tumor Size (mm) | | i.v. Challenge | | | | | |
|---|---|---|---|---|---|---|---|---|
| | | | UV2237m | | | K1735m2 | | |
| | UV2237m | K1735m2 | Lung Met. Med. (Range) | Lung Weight (mg,mean±SD) | | Lung Met. Med. (Range) | Lung Weight (mg,mean±SD) | |
| UV2237-cured | 0* | 9.2±5.3 | 0(0-0)* | 242 ±31 | | 191(107->200) | 770 ±306 | |
| K1735-cured | 6.0±4.3 | 0* | 140(84->200) | 847 ±230 | | 0(0-0)* | 228 ±22 | |
| Control | 12.6 ±1.3 | 15.3 ±3.0 | 167(93->200) | 898 ±227 | | >200(all>200) | 1079 ±110 | |

*:P<0.001 N=10

Established s.c. UV2237m or K1735m2 tumors in C3H/HeN mice were cured by intratumoral injections of lyophilized H5IFNβ (one injection for UV2237m, two injections at 1wk interval for K1735m2). 2 months later after disappearance of s.c. tumors, the cured mice were challenged either s.c. or i.v. with either UV2237m or K1735m2 cells. s.c. tumor sizes were measured 2 weeks later after inoculation. The i.v. challenged mice were killed 4 weeks later, the lungs were weighed and fixed in Bouin's solution and metastatic nodules were counted under a dissecting microscope.

FIG. 14

▼: one intralesional injection of insect cells

ADJUVANT PREPARATION FOR THE INDUCTION OF SPECIFIC IMMUNITY

This application claims benefit of priority to U.S. Provisional Application Ser. No. 60/208,436, filed on May 31, 2000.

The government owns rights in the present invention pursuant to grant number R35-CA42107 from the National Institutes of Health.

BACKGROUND OF THE INVENTION

A. Field of the Invention

The present invention relates generally to the fields of immunology and disease therapy. More particularly, it concerns the use of insect cell compositions as adjuvants to promote antigen specific immunological responses.

B. Description of Related Art

Methods for manipulating the immune system to achieve a desired effect have been known for many years, and are used both in the prevention and therapy of disease and in immunization protocols to generate specific antibodies for other uses, e.g., in diagnostics. However, generating an appropriate immune response is not always a straightforward matter. Particular problems arise with antigens that are "immunologically cryptic," in which cases the immune responses are often too weak to be of practical use.

The problems associated with generating immune responses apply to a wide range of clinical and laboratory protocols, with one of the most important areas being that of cancer treatment and therapy. Various modalities of therapy have been used during the past 30 years to treat cancer, including radiation and chemotherapy, radical surgery and immunologically-based protocols. Nevertheless, despite improvements in early diagnosis, surgical techniques and local and systemic therapies, most deaths from cancer result from metastases that are resistant to conventional therapies. Because systemic spread occurs early in the growth of many malignancies, surgery and radiotherapy may fail to achieve cure despite thorough eradication of the local disease. Chemotherapy is potent and systemic in its effects, but kills tumor cells by first-order kinetics so the last cancer cell may not be eliminated (Fidler, 1999). The goal of anti-cancer immunotherapy is the recruitment of the host immune system to destroy not only the primary neoplasm, but also any secondary metastatic cells. Cancer vaccines are mostly used for this purpose and are dependent on the presence of tumor-specific antigens and the ability to induce a cytotoxic immune response that recognizes tumor cells presenting antigens.

Tumor-associated antigens (TAAs) capable of being recognized by the cellular immune system (T-cells) have been identified. These antigens (also referred to as tumor associated or T-cell epitopes) include oncogene products activated by mutation and rearrangement (e.g., position 12 mutation in $p21^{ras}$; P210 product of bcr/abl rearrangement); mutated tumor-suppressor gene products (e.g., p53); reactivated embryonic gene products not expressed in adult tissues (e.g., P91A found in the P815 mastocytoma); MAGE 1 (found in melanomas and human breast tumors); tissue specific self-antigens expressed by tumors (e.g., tyrosinase); and a variety of others (Pardoll, 1993). Most tumor cell populations express certain common TAAs, but are heterogeneous with respect to the spectrum of TAAs that they express. Despite the array of tumor-associated T-cell epitopes expressed in tumors, tumor cells remain poorly immunogenic.

Thus, a major hurdle faced in the use of cancer vaccines is that many tumors, though potentially immunogenic, do not stimulate an effective antitumor immune response (Mueller, 1989). Most progressively growing neoplasms do not provoke immunological responses sufficient to control the growth of malignant cells, despite the fact that tumor cells express antigens which are recognizable as foreign by the immune system of the patient (Sibille et al., 1990).

Despite the continuing efforts in this field, it is apparent that improved methods and novel strategies for generating immune responses are still needed. Simple methods that are appropriate for use with a wide variety of antigens are particularly desirable. The development of a method by which to improve the immune response against immunologically cryptic antigens would represent a significant advance, particularly if such a method was adaptable for use against clinically relevant antigens.

SUMMARY OF THE INVENTION

The present invention addresses deficiencies in the art by disclosing compositions and methods for use of the adjuvant properties of insect cells. Insect cells provide the added capability of facilitating the expression heterologous proteins or peptides, for example, an antigen or an additional immunomodulator.

A particular embodiment of the instant invention therefore encompasses a method of invoking an immune response by administering an insect cell composition to a host. It is generally contemplated that the response that develops is antigen specific.

The instant invention facilitates the elicitation of an immune response. The antigen against which the response is developed may comprise any antigen to which such a response would be desirable. It is therefore specifically contemplated that the response would be directed against a pathogen or neoplastic antigen. In a particular embodiment, the antigen will be a tumor antigen.

In the context of the instant invention, it is contemplated that the insect cell composition administered to a host may consist of insect cells transformed with exogenous DNA. In a specific embodiment, the exogenous DNA will comprise a baculovirus expression vector. It is envisioned that the baculovirus expression vector may further comprise an exogenous construct. The exogenous construct may encode a cytokine, for example, interferon β, a tumor antigen, for example MAGE-1, MAGE-3, Melan-A, P198, P1A, gp100, TAG-72, $p185^{HER2}$, milk mucin core protein, carcinoembryonic antigen (CEA), P91A, p53, $p21^{ras}$, P210, BTA or tyrosinase, or a foreign antigen, including a pathogen specific antigen.

It is envisioned that a variety of insect cell species may be utilized in the context of the instant invention. In a specific embodiment, the cell composition of the instant invention may comprise *Spodoptera* or *Trichoplusia* cells. The cell composition may further be characterized as *Spodoptera frugiperda* cells or *Trichoplusia ni* cells.

It is contemplated that the organism or host to which the compositions will be administered will be a mammal. It is specifically contemplated that the compositions will be administered to a human or animal of commercial relevance. For the purpose of the instant invention, animals of commercial significance are domestic or agricultural species, including, for example primates, horses, cattle, pigs, goats, sheep, dogs, cats, mice, rats, rabbits and poultry. In a particular embodiment, the organism may be further characterized as a human.

The instant invention facilitates the creation of an antigen specific response to any type of pathogen or disease state in which such a response may be elicited. The host organism to whom the composition is administered may be naive or alternatively currently infected or diseased, or recovered from a past infection or disease state. In one embodiment, the host organism will have a tumor. It is envisioned that the composition of the instant invention may be introduced directly into the tumor to induce an immune response, potentially by injection. The composition may be administered more than once, and in a specific embodiment at least twice or thrice.

When administered to a host organism, it is envisioned that the insect composition of the instant invention will comprise a pharmaceutical composition. In one embodiment, the number of insect cell equivalents administered in a composition will be between $10^5$ and $10^7$. In alternate embodiments, the cells to be administered may be intact, disrupted, lyophilized, purified or freeze/thawed.

It is contemplated that the claimed compositions may be delivered as either a therapeutic or prophylactic treatment. One embodiment of the instant invention comprises administering to a mammal a therapeutically effective amount of a pharmaceutical composition comprising an insect cell composition. It is envisioned that the targeted tumor may be metastatic and administration of the disclosed composition will induce an immune response specific for metastatic tumor cells.

A further embodiment of the instant invention comprises a method of treating a mammal having a disease state by administering a therapeutically effective amount of a pharmaceutical composition comprising an insect cell composition to the mammal to induce an immune response against the disease state. While specific embodiments of the invention are particularly directed at the treatment of cancer, it is envisioned that the methods and compositions of the instant invention would be equally applicable to other disease states in which the elicitation of an antigen specific immune response is desirable.

It is further envisioned that the components necessary to perform the instant invention may be contained in a kit. In a preferred embodiment, the kit would comprise a pharmaceutical composition comprising insect cells for the induction of an immune response and a container for the composition.

In specific embodiments of the invention, it is desirable that the insect cells be inactivated prior to being administered to a host. The inactivation may occur by subjecting the cells to freeze-thaw cycles or other technique to achieve an analogous effect which will be well known to one of ordinary skill.

It is envisioned that the adjuvant preparations claimed by the instant application may be useful in vaccine preparations. Vaccine preparations of the invention may be formulated to be prophylactic or therapeutic. A person of ordinary skill in the art would recognize the types of different formulations, route and times of administration that would differentiate a therapeutic versus a prophylactic vaccine. A specific embodiment consists of a vaccine composition comprising an antigenic compound, insect cells and a pharmaceutically acceptable carrier. A further embodiment consists of methods of preparing vaccines including insect cells and at least one antigen in a pharmaceutically acceptable composition or accompanied by a pharmaceutically acceptable carrier.

It is further contemplated that the composition of the instant invention may be utilized for establishing immunological memory. This method encompasses providing a host with a pharmaceutical composition comprising an antigenic compound and insect cells. In a preferred embodiment, the instant invention facilitates the recruitment of immune cells to a specific site in a host by administering to the host a therapeutically effective amount of a pharmaceutical composition comprising an insect cell composition. The instant invention also facilitates the stimulation of immune cells in a similar manner. Stimulation with the adjuvant composition of the instant invention may be carried out either in vivo or in vitro.

A particular embodiment of the instant invention is a method of treating cancer comprising isolating cancer cells from a host, inactivating the cancer cells, and reintroducing the inactivated cancer cells into the host with an insect cell preparation in a pharmaceutical composition. This method may be further characterized as inactivating the cells by irradiation and preparing the cell suspension by admixing the tumor cells with the insect cell composition. Because the compositions and methods of the invention facilitate the development of a memory response, it is envisioned that the disclosed composition will be equally effective whether the cancer is localized or diffuse.

A further embodiment of the instant invention comprises a method of treating cancer comprising isolating cancer cells from a host, rendering the cancer cells inactive, isolating immune cells from the host, contacting the immune cells with a composition of inactive cancer cells and an insect cell composition, and re-administering to the host a pharmaceutical composition comprising the activated immune cells. Where the composition is administered to a host with cancer or a tumor, the composition may be further combined with an additional anti-cancer or anti-tumor therapy.

An additional embodiment is characterized as a method of inducing an immune response comprising isolating immune cells from a host, culturing and expanding the immune cells in vitro, contacting the cultured cells with an insect cell composition, wherein the insect cells have been transformed with a baculovirus expression system comprising an antigen gene, and reintroducing the immune cells into the host.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 13: Therapeutic vaccination with $H_5 IFN\beta$ against lung metastasis.

FIG. 14: Induction of specific tumor immunity in C3H mice cured of UV2237m or K1735m2 primary subcutaneous tumors.

DESCRIPTION OF ILLUSTRATIVE EMBODIMENTS

Figure 1:
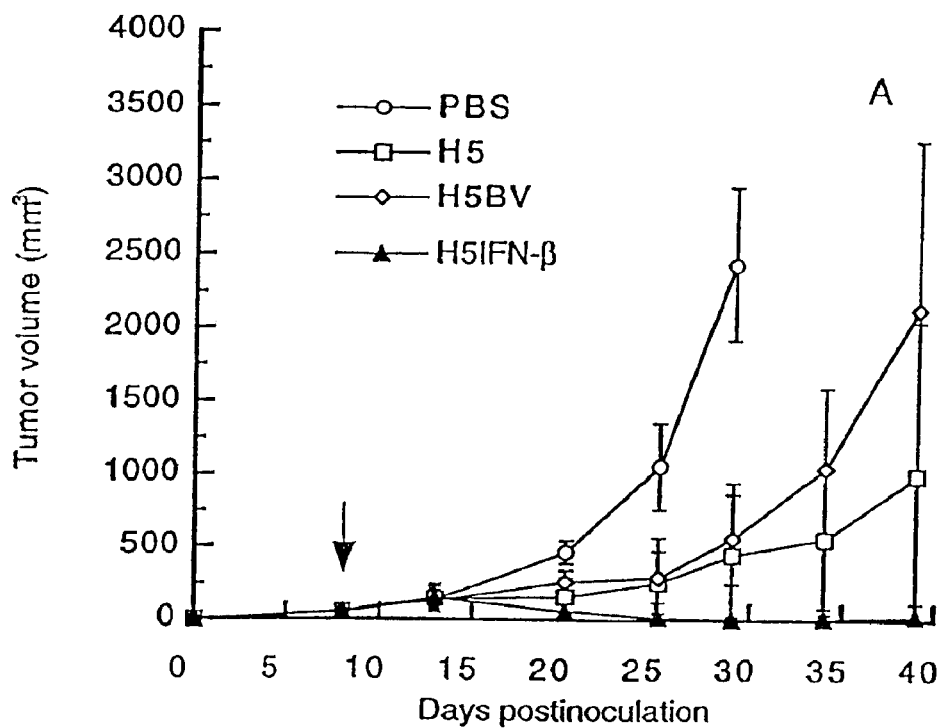
FIG. 1: Eradication of UV2237m fibrosarcoma by H5IFNβ: C3H/HeN mice were injected s.c. with $2\times10^5$ syngeneic UV-2237m fibrosarcoma cells. On day 8 (when tumors measured 5–6 mm in diameter), the tumors were injected once with 0.2 ml saline containing $2\times10^6$ H5 cells infected with BV (control) or $2\times10^5$ H5 IFNβ cells. Injection of H5 IFNβ led to complete regression of the s.c tumors.

Due to the nature of disease, it is frequently the organism, virus or cancerous cell that can successfully escape detection by the immune system that results in significant morbidity or mortality in a host. When the immune system successfully detects a pathogen or tumor cell it is generally quickly dispatched with little or no inconvenience to the host. Conversely, by evading detection, an agent has an opportunity to establish or sequester itself, making it much more difficult for the immune system to later overcome the infection, pathogen or neoplasia. The present invention contemplates the introduction of a composition with adjuvant properties into a host. This composition and methods for its administration function to prime the immune system to recognize specific agents and subsequently properly neutralize them. The invention facilitates not only the development of a strong primary immune response, but also the establishment of a potent memory response.

The present inventors have discovered that insect cell preparations possess adjuvant properties. Further, the combination of these compositions with specific immunomodulators results in a synergistic response. Immune cells contacted with insect cells or insect cell compositions as claimed become activated and proliferate in an antigen independent manner. A preferred embodiment of the present invention is therefore an adjuvant composition. In its simplest form, this composition comprises a pharmaceutically acceptable composition comprising intact insect cells or an extract thereof.

Most foreign compounds are antigenic and will induce an immune response when introduced into a naïve host. There are, however, a specific subset of compounds that specifically and preferentially result in the activation, proliferation and/or recruitment of immune cells or specific subsets of immune cells. These compounds are deemed adjuvants. Because certain adjuvants are able to recruit immune cells into an area and prime them for activation, they are often combined in vaccine formulations.

Adjuvants are traditionally defined as substances which augment, stimulate, activate, potentiate, or modulate the immune response at either the cellular or humoral level. While classical adjuvants were generally compositions comprising bacterial antigens, i.e., Freund's adjuvant, BCG, or *Corynebacterium parvum*, the purification and characterization of immunomodulators has led to an increased utilization of these molecules for their adjuvant properties. The mode of action of adjuvants may be either non-specific, i.e., resulting in increased immune responsiveness to a wide variety of antigens, or antigen-specific, i.e., affecting a restricted type of immune response to a narrow group of antigens.

The compositions and methods of the instant invention facilitate not only the activation and proliferation of immune cells but also their recruitment. Thus, administration of the compositions of the instant invention facilitate the migration of immune cells into a specific area, for example, a tumor where the immune cells may become activated and proliferate. While activation and proliferation in response to the adjuvant properties of the instant invention is non-specific, the presence of foreign antigen in the vicinity of the immune cells facilitates the progression to an antigen specific response.

While adjuvants have long been used to induce, enhance or potentiate an immune response, the subject matter of the instant invention provides an adjuvant composition possessing properties heretofore absent from other adjuvant compositions. The insect cell compositions of the instant invention have the added feature that they may contain vectors for the expression of exogenous proteins without impacting the immunomodulatory properties inherent in the cells. Insect cells transformed with exogenous DNA to express either antigenic proteins or other molecules of immunological relevance exhibit not only their immunomodulatory property but also facilitate the presentation of additional relevant molecules to immune cells within a single preparation.

It is envisioned that the adjuvant compositions and methods comprising insect cell are useful in a variety of conditions in which the induction or enhancement of an immune response is desired. Preferred embodiments of the invention thus comprise insect cells or insect cell extracts or a composition comprising insect cells or insect cell extracts and antigens, immunogens or immunomodulators administered to preferentially induce an immune response for controlling or combating disease, damage, injury, morbidity or mortality in a host organism.

There are two, basic alternate embodiments contemplated by the inventors. In one embodiment, insect cells or insect cell compositions are provided in a formulation without exogenous DNA. It is envisioned that such compositions may further comprise immunomodulators, antigens or antigenic preparations. In general, the compositions of the instant invention will comprise an insect cell composition in combination with an immunomodulator. The combination of the adjuvant properties of insect cells with the immunomodulator facilitates the development of a strong antigen specific immune response. While the invention demonstrates that the administration of an insect cell composition alone facilitates the creation of a strong response, and it is well known that the administration of specific immunomodulators effects a response, the combination of an insect cell composition with an immunomodulator results in a synergistic response that is markedly superior to the sum of the combination of the responses elicited by the individual elements. However, in a preferred embodiment of the invention, insect cells or an insect cell extract is introduced directly into a tumor of a host organism. This type of vaccination does not require the addition of other antigenic compounds or immunomodulators. The introduction of the insect cell composition facilitates the recruitment and activation of immune cells. The recruitment of immune cells into an area facilitates the destruction of the tumor and the induction of a memory response that prevents recurrence and also primes the system to handle metastatic cells. A person of ordinary skill would recognize that, depending upon the desired response, the insect cell compositions may be administered with or without antigen for the purpose of inducing the activation, proliferation or recruitment of immune cells in vivo or in vitro.

Beyond its use as a basic adjuvant, the instant invention has the added benefit that the formulation of insect cell compositions or insect cell extracts may be transformed with exogenous DNA. In this context, insect cell compositions transformed with an expression vector facilitate the expression of a protein of antigenic or immunological significance. Such a composition facilitates the combination of the adjuvant properties of the insect cells with the properties of the expressed antigen, immunogen or immunomodulator in a single formulation. Therefore, the desired immune reaction may be modulated by the transformation of the insect cells with a vector facilitating the expression of, for example, an interferon or interleukin, or directed by the transformation of the insect cells with a vector facilitating the expression of, for example a pathogenic or tumor antigen. It is generally contemplated that the protein expressed will be an immunomodulator. Nevertheless, embodiments are specifically contemplated in which the insect cells are engineered to express multiple exogenous proteins in which at least on of such proteins is an immunomodulator and at least one is an antigenic compound of interest. Embodiments are also contemplated in which exogenous immunomodulator protein is present in the composition and the insect cells are transformed with a construct encoding an antigenic construct.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. The benefit of the instant system is that when an immunogen is expressed in the context of the insect cell system, there is no longer a need to couple the antigen with a carrier molecule. Following expression, the insect composition may be placed in a pharmaceutical composition and introduced directly into the host. Vaccine preparations therefore require fewer processing steps.

The compositions and methods of the instant invention induce the activation and proliferation of immune cells both in vivo and in vitro. An insect cell or insect cell extract composition introduced into an in vitro culture of immunological cells activates the cells and induces them to proliferate. It is envisioned that these methods and preparations would be useful in the in vitro expansion of cultured immunological cells or immunological cell subsets (i.e., T cells, B cells or other professional Antigen Presenting Cells).

The invention is specifically conceived to address the problem of inducing immunity to neoplastic cells. While the compositions and methods effectively induce the recruitment, activation and proliferation of immune cells upon introduction into a tumor, the composition also facilitates the development of a strong memory response. The development of these memory cells facilitates the establishment of a strong anti-tumor immuno-surveillance network. The development of a strong memory response not only protects against subsequent related neoplasia but also facilitates the destruction of metastases of the primary tumor. While injection of the preparation may be sight specific, the response that ultimately develops attacks not only the primary tumor but also metastatic cells dispersed throughout the host.

A. Anti-Tumor Vaccination

Neoplastic or tumor cells generally express altered protein on their surface in the context of MHC CI that may be detected by the immune system as foreign thus leading to the induction of an immune response. Frequently, the difficulty in inducing an anti-tumor response is not in establishing that a tumor antigen is present and detectable by immune surveillance. Rather, the problem centers on recruiting the necessary cells to the area and providing the cells with the proper secondary signals necessary for the development of an effective immune response. The adjuvant properties of the instant invention initiate the recruitment of immune cells into the tumor and provide for the recognition of tumor antigens generally leading to the ultimate regression of the tumor. A further benefit is that tumor infiltration by lymphocytes facilitates the creation of memory cells. Thus, if tumor cells have metastasized or if the tumor recurs, a subpopulation of lymphocytes can readily be dispatched to deal with subsequent challenges or metastatic cells.

As previously discussed, the added benefit of the disclosed system is that the preparation may be engineered to further comprise recombinant proteins in a single composition. Thus, the tumor infiltration induced by the disclosed preparation may be further enhance by the inclusion of expressed antigen, immunogen or an immunomodulator. Therefore, in a preferred embodiment of the invention, the insect cell preparation is transformed with a expression vector, i.e., baculovirus comprising the gene for human IFNβ. A preparation of these cells may be directly introduced into the tumor, thus leading not only to the recruitment and potential activation of the immune cells by the adjuvant, but, in addition, the further benefit accorded by the inclusion of an secondary agent in the preparation.

It is contemplated that antitumor vaccination may occur by a variety of routes. In a preferred embodiment of the instant invention, an insect cell composition is injected directly into a tumor in order to induce the recruitment of immune cells. It is envisioned that the formulation may be untransformed cells or that the insect cells may also contain exogenous DNA and thus be capable of expressing protein of immunological relevance particularly immunomodulators capable of enhancing immune cell recruitment, activation or proliferation.

While direct tumor injection is specifically contemplated, antitumor vaccinations may occur through alternate routes. Where the composition is not introduced directly into the tumor it is generally contemplated that the composition will further consist of a an antigen composition, preferably a tumor antigen. This type of preparation is particularly contemplated for neoplasia in which the cancer is not localized or is currently at a late stage of metastases. For the purpose of this type of vaccination, the composition may be introduced in a manner that a person of ordinary skill would readily determine as most appropriate.

B. Insect Cells

The term "insect cells" means insect cells from the insect species which exhibit adjuvant properties when introduced into a host organism or when contacted by immune cells. In certain embodiments of the instant invention, it is contemplated that insect cells comprise cells which are subject to baculovirus infection. For example: *Autographa californica, Bombyx mori, Spodoptera frugiperda, Choristoneura fumiferana, Heliothis virescens, Heliothis zea, Orgyia pseudotsugata, Lymantira dispar, Plutelia xylostella, Malacostoma disstria, Trichoplusia ni, Pieris rapae, Mamestra configurata* and *Hyalophora cecropia*. See U.S. Pat. Nos. 5,498,540 and 5,759,809, incorporated herein by reference. In a particular embodiment, the insect cells are H5 insect cells (Invitrogen, Sorrento, Calif.), derived from *Trichoplusia ni*. Such insect cells may be used in an intact form, or may be used following lyophilization or freeze-thaw cycles.

It is envisioned that a number species of insects possess cells or cell extracts that when introduced into a mammalian host would exhibit classic adjuvant properties. It is further contemplated that it is well within the capabilities of a person of ordinary skill in the art to screen alternate species, not expressly disclosed herein, for such properties.

Insect cells may be cultured according to standard techniques, such as in IPL-41 medium (JRH Biosciences, Inc.) with or without 10% fetal calf serum (Hyclone Laboratories, Inc.) as described in U.S. Pat. No. 5,759,809. A exemplary procedure for suspension cell cultures of H5 cell is, in brief, as follows. Adherent H5 cells are transferred from tissue culture flasks into spinner flasks. Serum free medium (Excell 400 medium from JRH BioSciences) supplemented with heparin is used to reduce cell aggregation. The cells are grown for several passages until they are >95% viable and have a doubling time between 18 and 24 hours. At this point, the cells are weaned from heparin. If the cells continue to grow in suspension without the addition of heparin they may be indefinitely maintained as a suspension until transformation. An alternative procedure for culturing insect cells in media containing fish serum has recently been described. See U.S. Pat. No. 5,498,540, incorporated herein by reference. For embodiments requiring transformed cells, cultured insect cells may be transfected with recombinant baculovirus or other expression vectors by standard protocols. See, e.g., U.S. Pat. No. 5,759,809, incorporated herein by reference.

C. Baculovirus Expression Vectors

Because of the simplicity of technology, capacity for large inserts, high expression levels of biologically functional recombinant protein, and ease of purification, the baculovirus expression vector system (BEVS) is one of the most powerful and versatile eukaryotic expression systems available. Compared to other higher eukaryotic expression systems, the most distinguishing feature of BEVS is its potential to achieve high levels of expression of a cloned gene. Consequently, in situ inoculation of tumors with insect cells infected with recombinant baculovirus encoding immunomodulating cytokine genes should provide high local concentrations of cytokines to kill tumor cells and to elicit immune response, and should also enhance immunity per se since insect cells are heterologous to mammalian hosts.

1. Infection with Baculoviral Vectors

In certain embodiments of the invention, the nucleic acid encoding a selected non-surface expressed protein or peptide may be integrated into a baculovirus expression vector. Such vectors are useful tools for the production of proteins for a variety of applications (Summers and Smith, 1987; O'Reilly et al., 1992; also U.S. Pat. No. 4,745,051 (Smith and Summers), U.S. Pat. No. 4,879,236 (Smith and Summers), U.S. Pat. No. 5,077,214 (Guarino and Jarvis), U.S. Pat. No. 5,155,037 (Summers), U.S. Pat. No. 5,162,222, (Guarino and Jarvis), U.S. Pat. No. 5,169,784 (Summers and Oker-Blom) and U.S. Pat. No. 5,278,050 (Summers), each incorporated herein by reference). Baculovirus expression vectors are recombinant insect vectors in which the coding region of a particular gene of interest is placed behind a promoter in place of a nonessential baculoviral gene. The classic approach used to isolate a recombinant baculovirus expression vector is to construct a plasmid in which the foreign gene of interest is positioned downstream of the polyhedrin promoter. Then, via homologous recombination, that plasmid can be used to transfer the new gene into the viral genome in place of the wild-type polyhedrin gene (Summers and Smith, 1987; O'Reilly et al., 1992).

The resulting recombinant virus can infect cultured insect cells and express the foreign gene under the control of the polyhedrin promoter, which is strong and provides very high levels of transcription during the very late phase of infection. The strength of the polyhedrin promoter is an advantage of the use of recombinant baculoviruses as expression vectors because it usually leads to the synthesis of large amounts of the foreign gene product during infection.

*Autographa californica* multinucleocapsid nuclear polyhedrosis virus (AcMNPV) is unusual among baculoviruses because it displays a wider host range than most baculoviruses (Martignoni et al., 1982). AcMNPV is the most extensively studied baculovirus and its genome sequence is known (Ayres et al., 1994). It is distinguished by a unique biphasic life cycle in its lepidopteran host insect (reviewed in Blissard and Rohrmann, 1990). Infection produces high titers of two forms of progeny virus, budded virus (BV) and occlusion derived virus (ODV).

Two routes, adsorptive endocytosis (or viropexis) and direct fusion of BV envelope with plasma membrane, are proposed for entry of BV into cultured cells. Although BV may enter cells by fusion (Volkman et al., 1986), the majority of data indicates that the primary route is by adsorptive endocytosis (Charlton and Volkman, 1993).

2. Expression of Cloned Genes from Baculovirus Promoters and Enhancers

In certain aspects of the present invention, baculovirus vectors which are designed for the expression of a desired gene or genes are required. Thus, particular embodiments may require a selected nucleic acid segment to be operably linked to control sequences, such as promoters and enhancers. In the context of positioning nucleic acid segments and sequence regions in combination, the term "operably linked" will be understood to mean connected so as to form a single, contiguous nucleic acid sequence, wherein the promoters, enhancers and other control sequences are positioned and oriented in a manner to provide optimal expression of the gene. It will be understood that promoters are DNA elements which when positioned functionally upstream of a gene leads to the expression of that gene. Each heterologous gene in the vector of the present invention is functionally positioned downstream of a promoter element.

In transient systems, the gene of interest is introduced into the cell by infection with a recombinant virus, for example baculovirus. In the most widely used baculovirus systems, the gene of interest is under the control of the polyhedrin promoter. The polyhedrin promoter is a very late promoter, which means that the expression of the gene of interest does not start until the late phase of the baculovirus infection. The expression levels are high, but transient as the baculovirus infection eventually leads to cell death.

3. Baculoviral Promoters and Enhancers

There are four distinct phases of a baculovirus infection, termed immediate-early, delayed-early, late and very late. Therefore, different baculovirus genes may be classified according to the phase of the viral infection during which they are expressed. Also there are a class of genes which have been defined as early genes, which have not been subcatagorized as either immediate-early or delayed-early. Different classes of promoters control each class of gene.

Immediate early promoters are distinguished by needing only host cell factors to drive expression. Examples are the ie1 (Guarino and Summers, 1987), ieN ie2 (Carson et al., 1991) and ie0 promoters. Delayed early promoters are distinguished by needing only products of the immediate-early genes, in addition to host cell factors to drive expression. Examples are the 39K (Guarino and Smith, 1991) and gp64 (Blissard and Rohrmann, 1989; Whitford et al., 1989) promoters. Early promoters have not been placed into the specific immediate-early of delayed-early class. Examples include the DA26, ETL and 35K promoters.

Late promoters requires products of the delayed-early and immediate-early genes, as well as other host cell factors, to drive expression. Examples are the gp64 (Blissard and Rohrmann, 1989; Whitford et al., 1989) and capsid (p39; Thiem and Miller, 1989) promoters. Very late promoters requires a number of baculovirus gene products, in addition to other host cell factors, to drive expression. Examples of promoters from this class are the polyhedrin (Hooft van Iddekinge et al., 1983) and the p10 (Kuzio et al., 1984) promoters. The best characterized and most often used baculoviral promoter is the polyhedrin promoter. The use of the polyhedrin promoter is a preferred embodiment of the present invention.

Enhancers are DNA elements which can be positionally located to enhance transcription from a given promoter. Enhancers which are active in insect cells to drive transcription are preferred in the present invention. Preferred are viral enhancers, and most preferred are baculoviral enhancers. Examples of baculoviral enhancers include hr1, hr2, hr3, hr4 and hr5 (Guarino et al., 1986).

4. Marker Genes and Screening

In certain aspects of the present invention, specific cells may be tagged with specific genetic markers to provide information about the infected, transduced or transformed cells. Therefore, the present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

In other aspects of the present invention, a genetic marker is provided which is detectable by standard genetic analysis techniques, such as DNA amplification by PCR™ or hybridization using fluorometric, radioisotopic or spectrophotometric probes.

Exemplary marker genes encode enzymes such as esterases, phosphatases, proteases (tissue plasminogen activator or urokinase) and other enzymes capable of being detected by their activity, as will be known to those skilled in the art. Contemplated for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells.

Other examples are chloramphenicol acetyltransferase (CAT) which may be employed with a radiolabeled substrate, firefly and bacterial luciferase, and the bacterial enzymes β-galactosidase and β-glucuronidase. Other marker genes within this class are well known to those of skill in the art, and are suitable for use in the present invention.

Another class of marker genes which confer detectable characteristics on a host cell are those which encode polypeptides, generally enzymes, which render their transformants resistant against toxins. Examples of this class of marker genes are the neo gene (Colberre-Garapin et al., 1981) which protects against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978) and the enzyme HPRT, along with many others well known in the art (Kaufman, 1990).

D. Immune Response

The primary role of the subject matter of the instant invention is in the induction of an effective protective immune response. Nevertheless, a significant component of the claimed compositions is the ability of the composition to preferentially activate and induce the proliferation and or recruitment of immune cells. The adjuvant properties of an insect cell or insect cell extract composition facilitate just such an immunological response. Nevertheless it is envisioned that the compositions of the instant invention may further comprise both antigenic components and/or immunomodulators. The combination of an insect cell or insect cell extract composition with an antigenic agent or an immunomodulator will further facilitate the establishment of the desired immunological response and allow for the creation of immunological memory.

1. Antigens

In one aspect, the invention provides a molecule or compound comprising an antigenic or immunogenic epitope. Compounds or molecules comprising an immunogenic epitope are those agents capable of inducing an immune response. An "immunogenic epitope" is defined as a part of an agent that elicits an immune response when the whole agent is the immunogen. These immunogenic epitopes are generally confined to a few loci on the molecule. For the purposes of the instant invention, the term "immunogen" or "immunogenic epitope" is not confined to the induction of solely a humoral or solely a cellular response. Rather, the term is used to denote the capability of a compound, molecule or agent to induce either or both a cellular and a humoral immune response.

As to the selection of molecules, compounds or agents bearing an immunogenic epitope it is well known in that art that specific conformations preferentially lead to the induction of a specific form of immune response. For example, peptides capable of eliciting protein-reactive sera as frequently represented in the primary sequence of a protein, can be characterized by a set of simple chemical rules, and are confined neither to immunodominant regions of intact proteins (i.e., immunogenic epitopes) nor to the amino or carboxyl terminals. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

U.S. Pat. No. 4,554,101, (Hopp) incorporated herein by reference, teaches the identification and/or preparation of epitopes from primary amino acid sequences on the basis of hydrophilicity. Through the methods disclosed in Hopp, one of skill in the art would be able to identify epitopes from within an amino acid sequence.

Numerous scientific publications have also been devoted to the prediction of secondary structure, and/or to the identification of epitopes, from analyses of amino acid sequences (Chou and Fasman, 1974a,b; 1978a,b, 1979). Any of these may be used, if desired, to supplement the teachings of Hopp in U.S. Pat. No. 4,554,101.

Moreover, computer programs are currently available to assist with predicting immunogenic portions and/or epitopic core regions of proteins. Examples include those programs based upon the Jameson-Wolf analysis (Jameson and Wolf, 1988; Wolf et al., 1988), the program PepPlot® (Brutlag et al., 1990; Weinberger et al., 1985), and/or other new programs for protein tertiary structure prediction (Fetrow and Bryant, 1993). Another commercially available software program capable of carrying out such analyses is MacVector (IBI, New Haven, Conn.).

Because of the protein expressing capabilities of the insect cells of the instant invention, it will often be desirable to provide a composition in which the insect cells also encompass an protein expressed in the context of an expression vector. In such an embodiment, immunogenic epitope-bearing peptides and polypeptides of the invention designed according to the above guidelines preferably contain a sequence of at least seven, more preferably at least nine and most preferably between about 15 to about 30 amino acids. However, peptides or polypeptides comprising a larger portion of an amino acid sequence of a polypeptide of the invention, containing about 30 to about 50 amino acids, or any length up to and including the entire amino acid sequence of the functional protein also are considered epitope-bearing peptides or polypeptides of the invention and also are useful for inducing the desired immune response. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

While in preferred embodiments of the invention, proteins are expressed by the transformed cells within the insect cell composition, it is also contemplated that native proteins or peptides or proteins produced by other means may be combined with the insect cell composition. The epitope-bearing peptides and polypeptides of the invention may thus be produced by any conventional means for making peptides or polypeptides including recombinant. For instance, a short epitope-bearing amino acid sequence may be fused to a larger polypeptide which acts as a carrier during recombinant production and purification. Epitope-bearing peptides also may be synthesized using known methods of chemical synthesis. For instance, Houghten et al (1985) has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. (Houghten et al, 1986).

Immunogenic epitope-bearing peptides are identified according to methods known in the art. For instance, Geysen et al. (1984) discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. (1984) with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 and Geysen (1987) further describes this method of identifying a peptide bearing an immunogenic epitope of a desired protein.

The immunogen or antigenic agent of the instant invention is contemplated to be or be derived from an agent or pathogen that causes some form of damage, injury, harm, morbidity or mortality to the host. As a result, an immunogen need not be an external agent but may be either a transformed or neoplastic cell. Further, the immunogen or antigenic agent need not be a living pathogen. Therefore, while an immunogen or agent would clearly constitute a bacteria, rickettsial, fungi, algae, protozoan, metazoan, helminth, other pathogenic organism or derivative thereof, it is also envisioned that the term would encompass any toxin, poison, virus, virion, virioid, prion or compound capable of doing harm to the host or to which it would be desirable to direct an immune response against.

The instant invention provides an adjuvant formulation that the skilled artisan will recognize as applicable to any number of cancers. The adjuvant composition may be provided in a formulation in which tumor antigens are either admixed with the insect cells or insect cell compositions or wherein the tumor antigen is expressed by the insect cells to be administered. An example of tumor antigens specifically contemplated for use in the context of the instant invention include MAGE-1, MAGE-3, Melan-A, P198, P1A, gp100, TAG-72, $p185^{HER2}$, milk mucin core protein, carcinoembryonic antigen (CEA), P91A, p53, $p21^{ras}$, P210, BTA and tyrosinase. Table 1 sets forth a more extensive, exemplary list of tumor antigens that may be employed in the context of the invention.

TABLE 1

Marker Antigens of Solid Tumors

| Tumor Site | Antigen Identity/Characteristics |
|---|---|
| A: Gynecological | |
| GY | 'CA 125' >200 kD mucin GP |
| ovarian | 80 Kd GP |
| ovarian | 'SGA' 360 Kd GP |
| ovarian | High $M_r$ mucin |
| ovarian | High $M_r$ mucin/glycolipid |
| ovarian | NS |
| ovarian | NS |
| ovarian | High $M_r$ mucin |
| ovarian | High $M_r$ mucin |
| GY | 7700 Kd GP |
| ovarian | 'gp 68' 48 Kd GP |
| GY | 40, 42 kD GP |
| GY | 'TAG-72' High $M_r$ mucin |
| ovarian | 300–400 Kd GP |
| ovarian | 60 Kd GP |
| GY | 105 Kd GP |
| ovarian | 38–40 kD GP |
| GY | 'CEA' 180 Kd GP |
| ovarian | CA 19-9 or GICA |
| ovarian | 'PLAP' 67 Kd GP |
| ovarian | 72 Kd |
| ovarian | 69 Kd PLAP |
| ovarian | unknown $M_r$ PLAP |
| ovarian | $p185^{HER2}$ |
| uterus ovary | HMFG-2 |
| GY | HMFG-2 |
| B: BREAST | 330–450 Kd GP |
| | NS |
| | 37 kD |
| | NS |
| | NS |
| | 47 Kd GP |
| | High $M_r$ GP |
| | High $M_r$ GP |
| | NS |
| | NS |
| | 1 (Ma) blood group Ags |
| | NS |
| | oestrogen receptor |
| | EGF Receptor |
| | Laminin Receptor |
| | erb B-2 p185 |
| | NS |
| | 126 Kd GP |
| | NS |
| | NS |
| | 95 Kd |
| | 100 Kd |
| | NS |
| | 24 Kd |
| | 90 Kd GP |
| | CEA & 180 Kd GP |
| | colonic & pancreatic mucin similar to Ca 19-9 |
| | milk mucin core protein |
| | milk mucin core protein |
| | affinity-purified milk mucin |
| | $p185^{HER2}$ |
| | CA 125 >200 Kd GP |
| | High $M_r$ mucin/glycolipid |
| | High $M_r$ mucin |
| | 'gp48' 48 Kd GP |
| | 300–400 Kd GP |
| | 'TAG-72' high $M_r$ mucin |
| | 'CEA' 180 Kd GP |
| | 'PLAP' 67 Kd GP |
| | HMFG-2 >400 Kd GP |
| | NS |
| C: COLORECTAL | TAG-72 High $M_r$ mucin |
| | GP37 |
| | Surface GP |
| | CEA |
| | CEA |

TABLE 1-continued

Marker Antigens of Solid Tumors

| Tumor Site | Antigen Identity/Characteristics |
|---|---|
| | cell surface AG |
| | secretory epithelium |
| | surface glycoprotein |
| | NS |
| | NS |
| | NS |
| | cell membrane & cytoplasmic Ag |
| | CEA & vindesine |
| | gp72 |
| | high $M_r$ mucin |
| | high $M_r$ mucin |
| | CEA 180 Kd GP |
| | 60 Kd GP |
| | CA-19-9 (or GICA) |
| | Lewis a |
| | Lewis a |
| | colonic mucus |
| D: MELANOMA | p97$^a$ |
| | p97$^a$ |
| | p97$^b$ |
| | p97$^c$ |
| | p97$^c$ |
| | p97$^d$ |
| | p97$^e$ |
| | p155 |
| | $G_{D3}$ disialogan-glioside |
| | p210, p60, p250 |
| | p280 p440 |
| | GP 94, 75, 70 & 25 |
| | P240–P250, P450 |
| | 100, 77, 75 Kd |
| | 94 Kd |
| | 4 GP chains |
| | GP 74 |
| | GP 49 |
| | 230 Kd |
| | 92 Kd |
| | 70 Kd |
| | HMW MAA similar to 9.2.27 AG |
| | HMW MAA similar to 9.2.27 AG |
| | GP95 similar to 376.96S 465.12S |
| | GP125 |
| | CD41 |
| E: GASTROINTESTINAL Pancreas, stomach | high $M_r$ mucin |
| gall bladder, pancreas, stomach | high $M_r$ mucin |
| Pancreas | NS |
| Pancreas, stomach, oesophagus | 'TAG-72' high $M_r$ mucin |
| Stomach | 'CEA' 180 Kd GP |
| Pancreas | HMFG-2 >400 Kd GP |
| G.I. | NS |
| Pancreas, stomach | CA 19-9 (or GICA) |
| Pancreas | CA125 GP |
| F: LUNG non-small cell lung carcinoma | p185$^{HER2}$ |
| | high $M_r$ mucin/glycolipid |
| | 'TAG-72' high $M_r$ mucin |
| | high $M_r$ mucin |
| | 'CEA' 180 kD GP |
| Malignant Gliomas | cytoplasmic antigen from 85HG-22 cells |
| | cell surface Ag from 85HG-63 cells |
| | cell surface Ag from 86HG-39 cells |
| | cell surface Ag from 86HG-39 cells |
| G: MISCELLANEOUS small round cell tumors | p53 |
| Medulloblastoma neuroblastoma rhabdomyosarcoma | neural cell adhesion molecule |
| Neuroblastoma | |
| renal cancer & glioblastomas | p155 |
| Bladder & laryngeal cancers | "Ca Antigen" 350–390 kD |
| Neuroblastoma | GD2 |
| Prostate | gp48 48 kD GP |

TABLE 1-continued

Marker Antigens of Solid Tumors

| Tumor Site | Antigen Identity/Characteristics |
|---|---|
| Prostate | 60 kD GP |
| Thyroid | 'CEA' 180 kD GP |

2. Immunomodulators

In another aspects of the invention, it is contemplated that the insect cell composition may further comprise a therapeutically effective composition of an immunomodulator. It is envisioned that an immunomodulator would constitute a cytokine, hematapoietin, colony stimulating factor, interleukin, interferon, growth factor or combination thereof. As used herein certain embodiments, the terms "cytokine" are the same as described in U.S. Pat. No. 5,851,984, incorporated herein by reference in its entirety, which reads in relevant part:

"The term 'cytokine' is a generic term for proteins released by one cell population which act on another cell as intercellular mediators. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-.alpha. and -.beta.; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-11, IL-12; IL-13, IL-14, IL-15, IL-16, IL-17, IL-18, LIF, G-CSF, GM-CSF, M-CSF, EPO, kit-ligand or FLT-3. As used herein, the term cytokine includes proteins from natural sources or from recombinant cell culture and biologically active equivalents of the native sequence cytokines.

3. β-Interferon

β-interferon (IFN-β) is low molecular weight protein that is produced by many cell types, including epithelial cells, fibroblasts and macrophages. Cells that express endogenous IFN-β are resistant to viral infection and replication. The β-interferon genes from mouse (GenBank accession numbers X14455, X14029) and human (GenBank accession numbers J00218, K00616 and M11029) have been isolated and sequenced. IFN-β is a multifunctional glycoprotein that can inhibit tumor growth both directly, by suppressing cell replication and inducing differentiation or apoptosis and indirectly by activating tumoricidal properties of macrophages and NK cells, by suppressing tumor angiogenesis and by stimulating specific immune response.

4. Interleukin-2

Interleukin-2 (IL-2), originally designated T-cell growth factor I, is a highly proficient inducer of T-cell proliferation and is a growth factor for all subpopulations of T-lymphocytes. IL-2 is an antigen independent proliferation factor that induces cell cycle progression in resting cells and thus allows clonal expansion of activated T-lymphocytes. Since freshly isolated leukemic cells also secrete IL-2 and respond to it IL-2 may function as an autocrine growth modulator for these cells capable of worsening ATL. IL-2 also promotes the proliferation of activated B-cells although this requires the presence of additional factors, for example, IL4. In vitro IL-2 also stimulates the growth of oligodendroglial cells. Due to its effects on T-cells and B-cells IL-2 is a central regulator of immune responses. It also plays a role in anti-inflammatory reactions, in hematopoiesis and in tumor surveillance. IL-2 stimulates the synthesis of IFN-γ in peripheral leukocytes and also induces the secretion of IL-1, TNF-α and TNF-β. The induction of the secretion of tumoricidal cytokines, apart from the activity in the expansion of LAK cells, (lymphokine-activated killer cells) are probably the main factors responsible for the antitumor activity of IL-2.

5. GM-CSF

GM-CSF stimulates the proliferation and differentiation of neutrophilic, eosinophilic, and monocytic lineages. It also functionally activates the corresponding mature forms, enhancing, for example, to the expression of certain cell surface adhesion proteins (CD-11A, CD-11C). The overexpression of these proteins could be one explanation for the observed local accumulation of granulocytes at sites of inflammation. In addition, GM-CSF also enhances expression of receptors for fMLP (Formyl-Met-Leu-Phe) which is a stimulator of neutrophil activity.

6. Induction of an Immune Response

Alternatively, cells, preferably peripheral blood mononuclear cells, are removed from a host and stimulated in vitro with an insect cell composition and an antigen (including a tumor antigen). Upon generation of an antigen-specific immune response, such as a CTL response, the cells may be expanded and reinfused into the patient.

E. Pharmaceutically Acceptable Carriers

Aqueous compositions of the present invention comprise an effective amount of insect cells or insect cell extracts dissolved or dispersed in a pharmaceutically acceptable carrier or aqueous medium. The phrases "pharmaceutically and pharmacologically acceptable" refer to molecular entities or compositions that do not produce an adverse, allergic or other untoward reaction when administered to an animal, or a human as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The active compounds may generally be formulated for parenteral administration, e.g., formulated for injection via the intravenous, intramuscular, sub-cutaneous, intralesional, and/or even intraperitoneal routes. The preparation of an aqueous compositions that contain an effective amount of insect cells or insect cell extracts as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; the preparations can also be emulsified.

The pharmaceutical forms suitable for injectable use include sterile aqueous solutions or dispersions; formulations including sesame oil, peanut oil or aqueous propylene glycol; or sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, or mixtures thereof, and in oils. Under ordinary conditions of storage and use, these preparations contain a preservative to prevent the growth of microorganisms.

Insect cells or insect cell extracts of the present invention can be formulated into a composition in a neutral and/or salt form. Pharmaceutically acceptable salts, include the acid addition salts (formed with the free amino groups of the protein) which are formed with inorganic acids such as, for example, hydrochloric and phosphoric acids, and such organic acids as acetic, oxalic, tartaric, mandelic, and the like. Salts formed with the free carboxyl groups can also be derived from inorganic bases such as, for example, sodium, potassium, ammonium, calcium, ferric hydroxides, or such organic bases as isopropylamine, trimethylamine, histidine, procaine and the like. In terms of using peptide as active ingredients, the technology of U.S. Pat. Nos. 4,608,251; 4,601,903; 4,599,231; 4,599,230; 4,596,792; and 4,578,770, each incorporated herein by reference, may be used.

The carrier can also be a solvent or dispersion medium containing, for example, water, ethanol, polyol (for example, glycerol, propylene glycol, and liquid polyethylene glycol, and the like), suitable mixtures thereof, or vegetable oils. The proper fluidity can be maintained, for example, by the use of a coating, such as lecithin, by the maintenance of the required particle size in the case of dispersion, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars and sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying or freeze-drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation or in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary, and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution or added to 1000 ml of hypodermoclysis fluid, and injected at the proposed site of infusion, (see for example, "Remington's Pharmaceutical Sciences" 15th Edition, pages 1035-1038 and/or 1570–1580). Some variation in dosage will necessarily occur depending on the condition of the subject being treated. The person responsible for administration will, in any event, determine the appropriate dose for the individual subject.

The insect cells or insect cell extracts may be formulated within a therapeutic mixture to comprise about 0.0001 to 1.0 milligrams, about 0.001 to 0.1 milligrams, about 0.1 to 1.0 or even about 10 milligrams per dose or so. Multiple doses can also be administered.

In addition to the compounds formulated for parenteral administration, such as intravenous and intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and include, for example, antibiotics and antihistamines.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations and powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions or preparations should contain at least 0.1% of active compound. The percentage of the compositions or preparations may, of course, be varied and may conveniently be between about 2 to about 75% of the weight of the unit, and preferably between 25–60%. The amount of active compounds in such therapeutically useful compositions is such that a suitable dosage will be obtained.

In certain embodiments, the use of lipid formulations and/or nanocapsules is contemplated for the introduction of insect cell or insect cell extract compositions into host cells.

Nanocapsules can generally entrap compounds in a stable andr reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be easily made.

In a preferred embodiment of the invention, the insect cells or insect cell extract composition may be associated with a lipid. The insect cells or insect cell extract composition associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The insect cells or insect cell extract composition associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes.

Phospholipids may be used for preparing the liposomes according to the present invention and may carry a net positive, negative, or neutral charge. Diacetyl phosphate can be employed to confer a negative charge on the liposomes, and stearylamine can be used to confer a positive charge on the liposomes. The liposomes can be made of one or more phospholipids.

A neutrally charged lipid can comprise a lipid with no charge, a substantially uncharged lipid, or a lipid mixture with equal number of positive and negative charges. Suitable phospholipids include phosphatidyl cholines and others that are well known to those of skill in the art.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C.

Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; or by transfer of liposomal lipids to cellular or subcellular membranes, or vice versa, without any association of the liposome contents. Varying the liposome formulation can alter which mechanism is operative, although more than one may operate at the same time.

In certain embodiments of the invention, the lipid may be associated with a hemagglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques. In one embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287–341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

A pharmaceutical composition comprising the liposomes will usually include a sterile, pharmaceutically acceptable carrier or diluent, such as water or saline solution.

F. Kits

Therapeutic or prophylactic kits of the present invention are kits comprising insect cells or insect cell extract composition. Such kits will generally contain, in suitable container means, a pharmaceutically acceptable formulation of insect cells or insect cell extract composition in a pharmaceutically acceptable formulation. The kit may have a single container means, or it may have distinct container means for each compound.

When the components of the kit are provided in one or more liquid solutions, the liquid solution is an aqueous solution, with a sterile aqueous solution being particularly preferred. The insect cells or insect cell extract composition may also be formulated into a syringeable composition. In which case, the container means may itself be a syringe, pipette, or other such like apparatus, from which the formulation may be applied to an infected area of the body, injected into an animal, and even applied to or mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the insect cells or insect cell extract composition formulation are placed, preferably, suitably allocated. The kits may also comprise a second container means for containing a sterile, pharmaceutically acceptable buffer or other diluent.

The kits of the present invention also will typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the injection/administration or placement of the ultimate insect cells or insect cell extract composition within the body of an animal. Such an instrument may be a syringe, pipette, forceps, and any such medically approved delivery vehicle.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
One Injection of H5IFN-β Eradicated UV2237M Tumors

Figure 2:
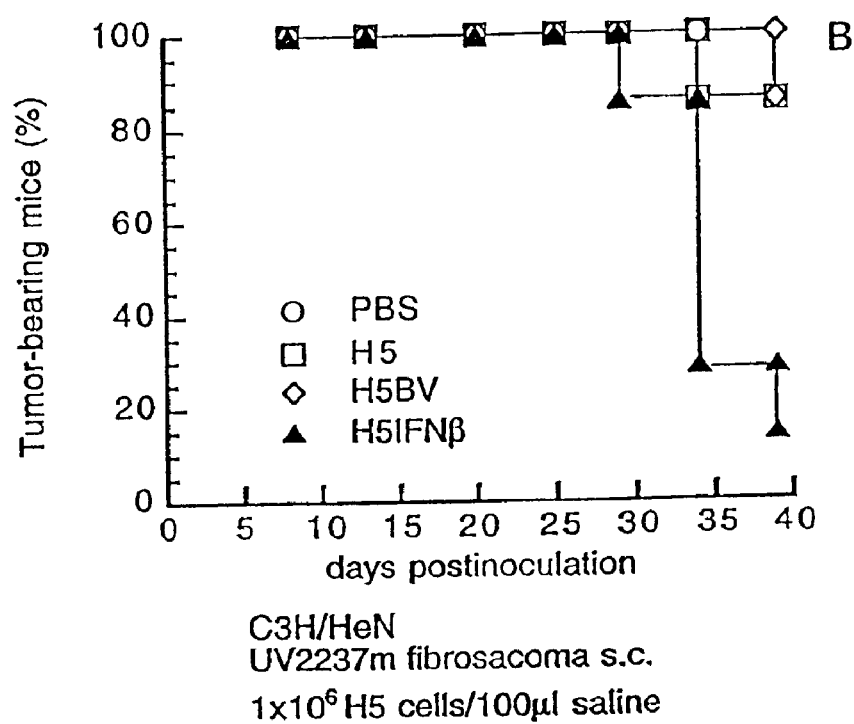
FIG. 2: UV2237m Tumor incidence after H5IFNβ treatment: The single intratumoral injection of $2\times10^6$ H5 IFNβ cells produced eradication of tumors in 9 of 10 C3H/HeN mice.

In initial experiments to assess the antitumor efficacy of H5IFN-β in vivo, live H5 cells with or without IFN-β were used. Complete eradication of tumors occurred in 70–90% of mice receiving one single intralesional injection of $H_5IFN-\beta$, tumor progression in the rest of the mice was also significantly suppressed. Tumor regression was noted in only 10–30% of mice receiving H5 alone or H5BV, and tumor growth in the rest of mice was slightly or moderately inhibited (FIGS. 1 and 2). These results suggest that intratumoral injection of H5IFN-β cells can eradicate established tumors. Adenoviruses encoding IFN-β gene were also used to eradicate UV2237m tumors of an average diameter of 5-mm, at least 4 intratumoral injections of $5 \times 10^8$ PFU recombinant adenoviruses were needed for complete regression.

Figure 3:
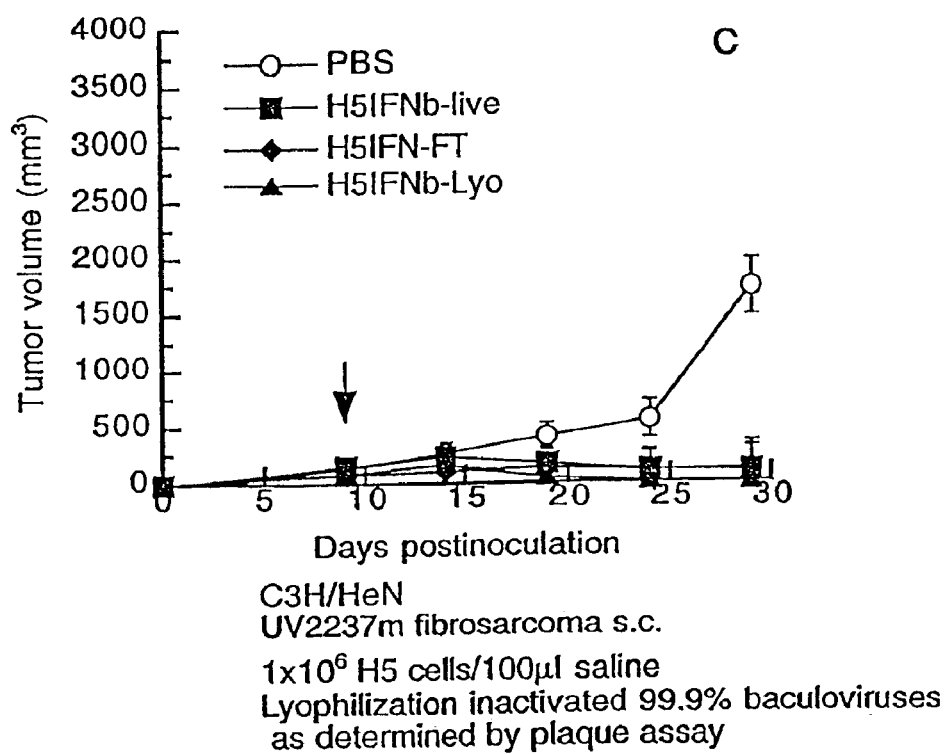
FIG. 3: Effect of viability of H5 on UV2237m fibrosarcoma growth: C3HeN mice were injected s.c. with $2\times10^5$ UV2237m fibrosarcoma cells. On day 9 (tumor diameter of 5–6 mm), the tumors were injected once with $2\times10^6$ live, frozen-thawed, or lyophilized H5 IFNβ cells. All treatment produced regression of s.c. tumors.

Example 2
Live H5IFN-β Cells are not Necessary to Produce Regression of Tumors Although members of the baculoviridae family only infect arthropods, baculoviruses are very easy to inactivate in vivo via fixation by the complement system. [$^{125}$I]IdUrd-labeled H5 cells showed that 95% live H5 cells could not survive longer than 24 h in vivo. Studies were nevertheless designed to determine whether live H5IFN cells and live baculovirus were necessary to eradicate subcutaneous UV2237m tumors. Live, lyophilized, or frozen-and-thawed (by freezing and thawing the cells thrice) H5IFN-β cells ($10^6$ cells/injection) were administered intratumorally. There appeared to be no difference in therapeutic benefit in mice treated with live, lyophilized, or frozen-and-thawed H5IFN-β cells (FIG. 3). Other experiments showed that lyophilization kept IFN-β activity intact, inactivated more than 99.9% baculoviruses as indicated by plaque assay, killed all H5IFN-β cells checked after resuspension in PBS solution and allowed the cells to be stored for an extended time period. Therefore, the lyophilized H5IFN-β cells were chosen for further studies. The protein contents for lyophilized $H_5$ and H5IFN-β cells were also investigated, and determined to be $0.27 \pm 0.05$ mg/$10^6$ cells and $0.3 \pm 0.06$ mg/$10^6$ cells, respectively.

Example 3
Optimal Dose of H5IFN-β Cells

Figure 4:
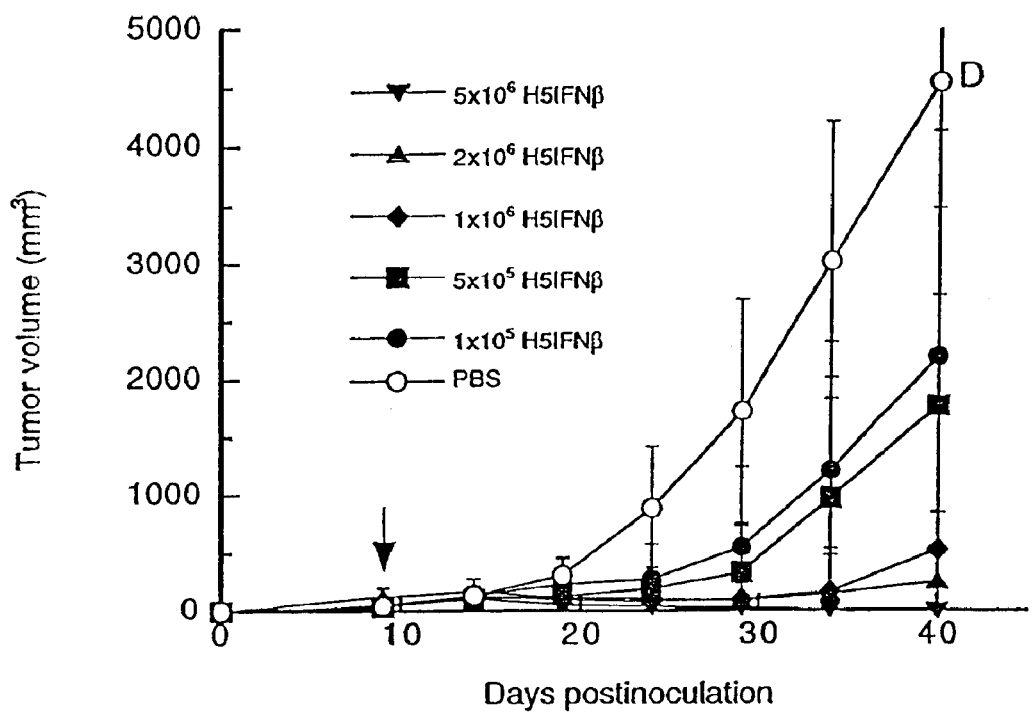
FIG. 4: Dose response curve for H5IFNβ: C3H/Hen mice were injected s.c. with $2\times10^5$ syngeneic UV-2237m fibrosarcoma cells. On day 9 (tumor diameter of 5–6 mm), a single intratumoral injection of different numbers of lyophilized H5 IFNβ cells was given. Either $5 \times 10^6$ or $2 \times 10^6$ cells produced regression of the tumors.

The minimal and optimal doses of H5IFN-β required to eradicate established UV2237m tumors were next determined. C3H/HeN mice were subcutaneously inoculated with UV2237m cells to form solid tumors of 4–6 mm in diameter. The tumor-bearing mice were treated by a single intralesional injection of escalating doses equivalent to $10^5$–$5 \times 10^6$ cells/mouse, of lyophilized H5IFN-β cells as determined by protein concentrations. FIG. 4 shows that the treatment with H5IFN-β caused regression of the tumors in a dose-dependent manner. Complete eradication of tumors occurred in 80–100% of mice receiving $1 \times 10^6$, $2 \times 10^6$, or $5 \times 10^6$ lyophilized H5IFN-β cells. $2 \times 10^6$ or $5 \times 10^6$ lyophilized H5IFN-β cells/mouse seemed to have more therapeutic benefit than $1 \times 10^6$ lyophilized H5IFN-β cells. Therefore, the dose of $2 \times 10^6$ was chosen for further studies.

Example 4
IFN-β is Necessary for Regression of Neoplasms

Figure 5:
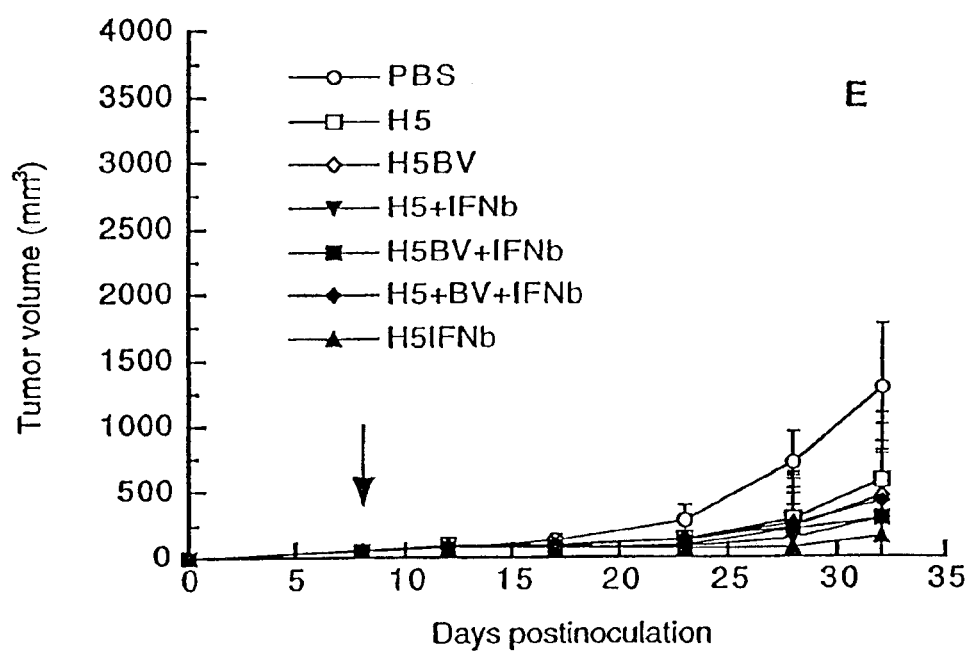
FIG. 5: The role of IFNβ in tumor regression: In these studies, recombinant murine IFNβ was admixed with H5 cells prior to injection into s.c. UV-2237m tumors. The presence of IFNβ (produced by H5 cells or admixed with H5 cells) produced regression of the tumors.

To more rigorously explore whether IFN-β is necessary for H5IFN-β therapy, UV2237m tumors of an average diameter of 4–6 mm were treated by a single intratumoral injection with 100 μl PBS, $2 \times 10^6$ H5IFN-β, $2 \times 10^6$ H5 cells alone, $2 \times 10^6$ H5 cells+$2 \times 10^7$ wild baculoviruses (the equivalent amount of baculoviruses contained in $2 \times 10^6$ H5IFN-β)+$2 \times 10^4$ Units IFN-β, $2 \times 10^6$ $H_5BV$, or $2 \times 10^6$ $H_5BV$+$2 \times 10^4$ Units IFN-β in 100 μl PBS. Complete regression of tumors occurred in 85.7% of mice receiving H5IFN-β or $H_5BV$+IFN-β only in 28.6% of mice receiving H5, in 42.9% in mice receiving $H_5BV$, in 57% of mice receiving H5+IFN-β or H5+BV+IFN-β (FIG. 5). These results indicate that provision of IFN-β is necessary for eradicating established tumors.

Example 5
T Cell-Mediated Tumor Regression

Figure 6:
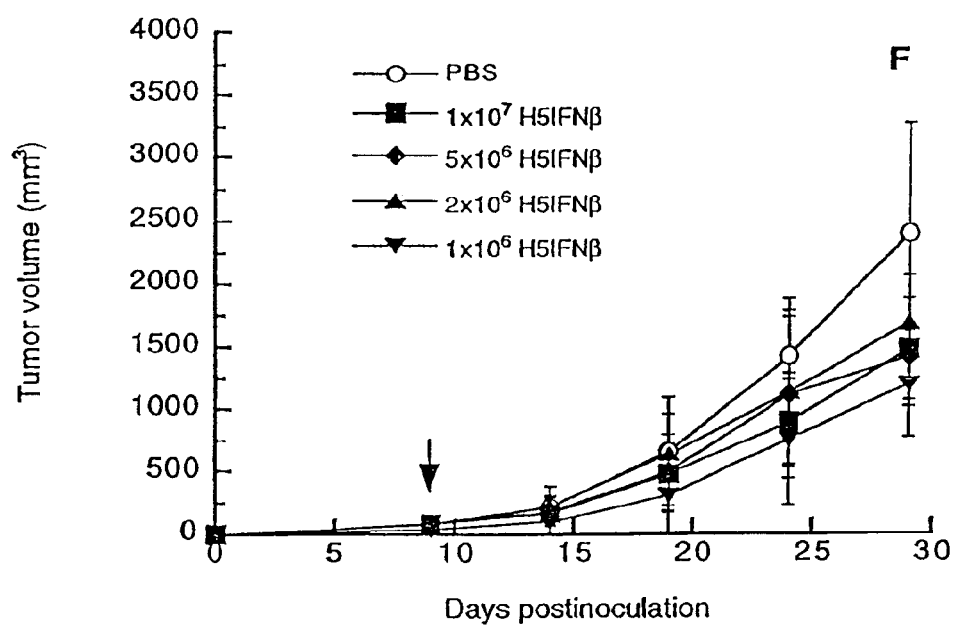
FIG. 6: UV2237m tumors in BALB/c nude mice: BALB/c nude mice were injected s.c with $1 \times 10^5$ UV-2237M fibrosarcoma cells. On day 9, the tumors (5–6 mm in diameter) were injected with $1 \times 10^6$, $2 \times 10^6$, $5 \times 10^6$ or $1 \times 10^7$ lyophilized $H_5 IFN\beta$ cell equivalents. No regressions were observed.

To evaluate the potential role of T cells in the H5IFN-β-induced tumor eradication, the antitumor efficacy of intratumoral H5IFN-β inoculation was tested in athymic nude mice (FIG. 6). High doses of H5IFN-β only caused a slight growth inhibition of the H5IFN-β-inoculated tumors compared with the PBS-inoculated tumors. This study suggests that direct cytopathic effects of H5IFN-β on the tumor cells do not play the major role in eradicating tumors, T cells are required for the antitumor effects of H5IFN-β.

Figure 7:
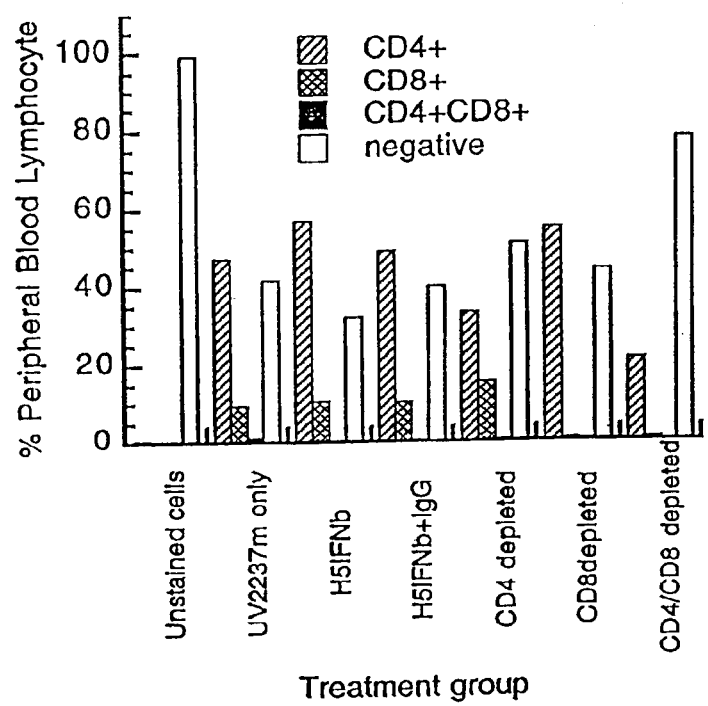
FIG. 7: Depletion of circulating CD4+ or CD8+ cells in C3H/HeN mice treated with αCD4 and αCD8 antibodies: C3H/HeN mice were treated with αCD4 or αCD8 antibodies (IgG served as control) 12 days prior to the collection of blood. Treatment with αCD4 and αCD8 depleted the lymphocytes.
Figure 8:
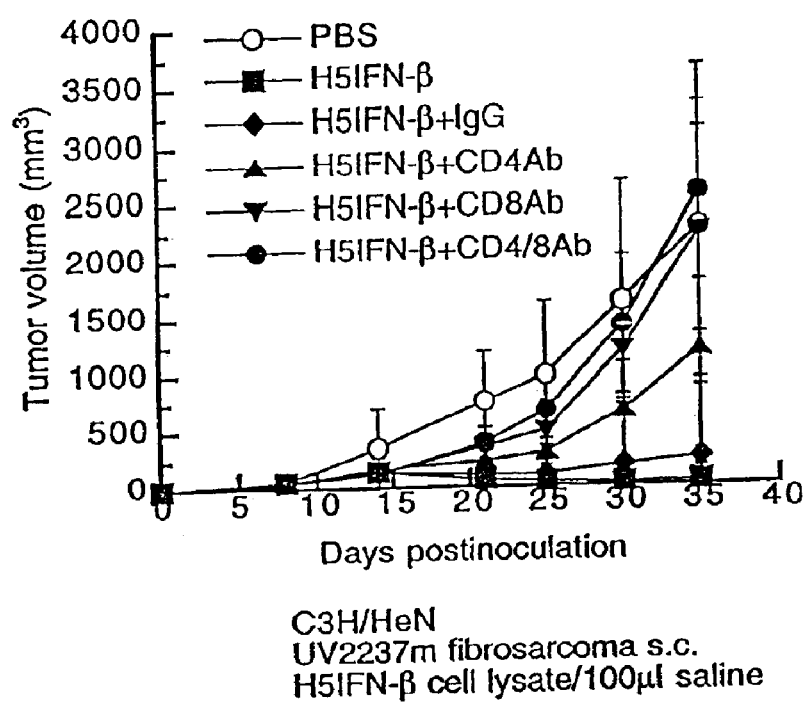
FIG. 8: T cell dependent UV2237m tumor eradication by $H_5 IFN\beta$.
Figure 9:
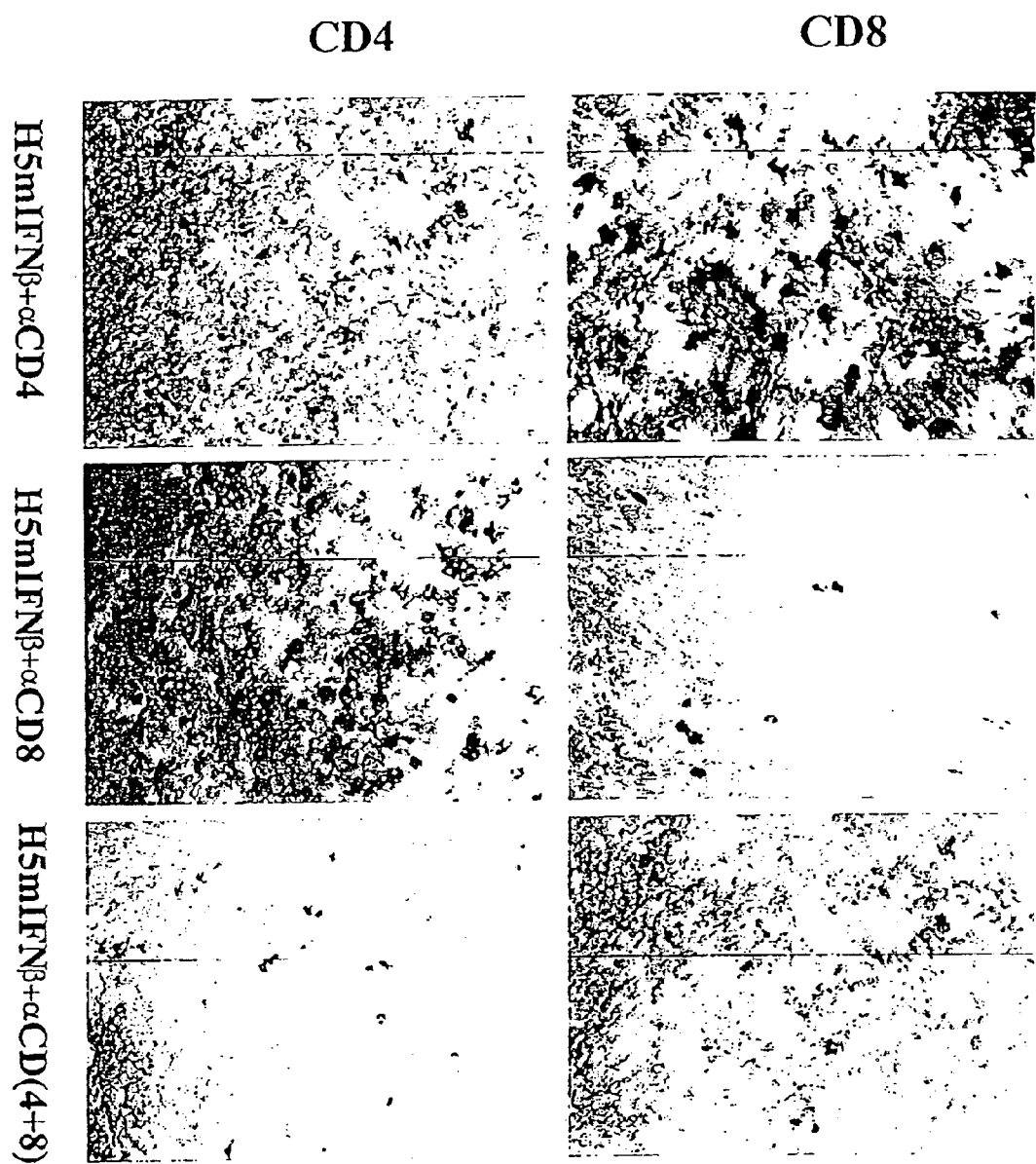
FIG. 9: Immunohistochemistry demonstrating tumor infiltration by CD4+ and CD8+ lymphocytes.
Figure 10:
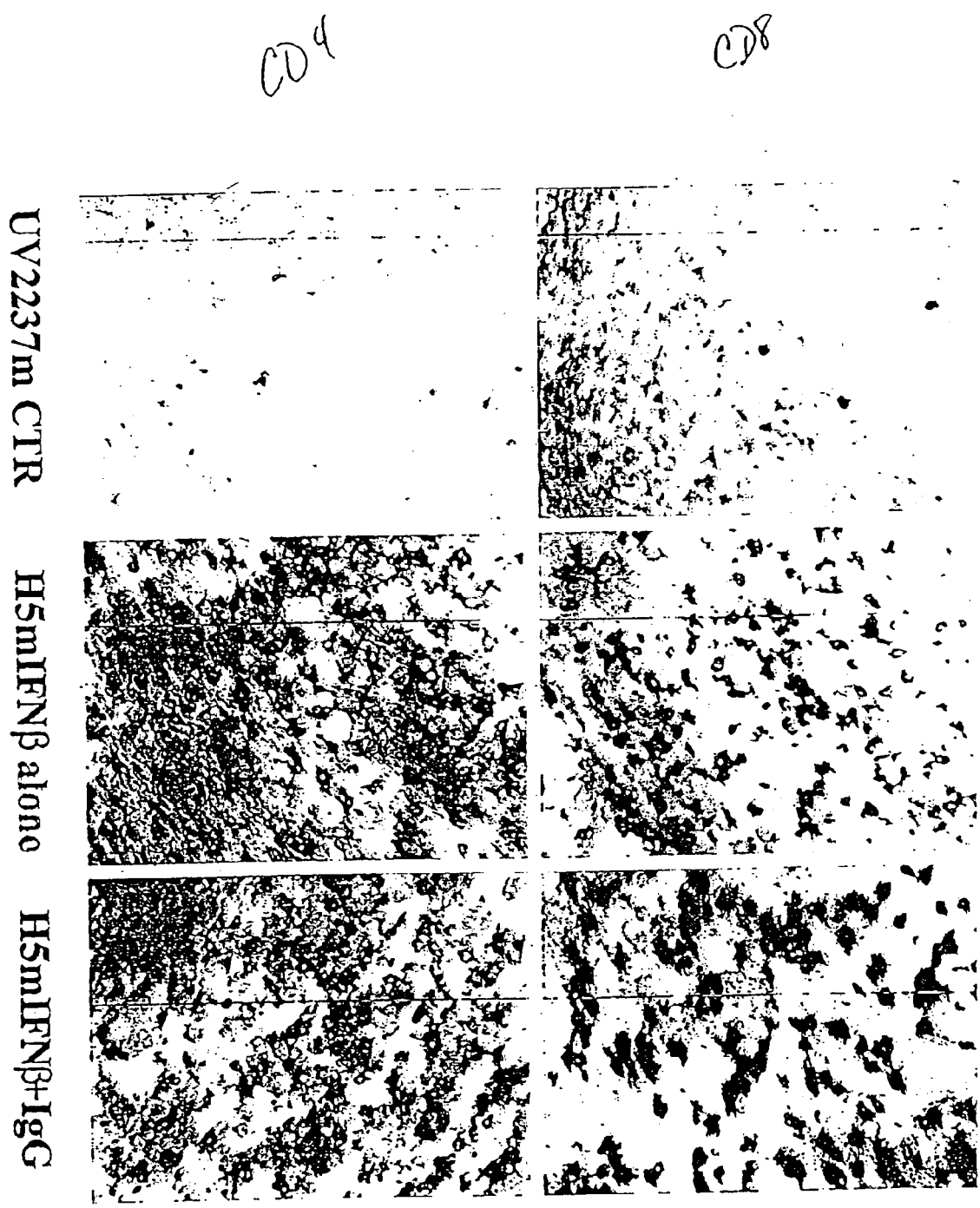
FIG. 10: Immunohistochemistry demonstrating tumor infiltration by CD4+ and CD8+ lymphocytes.

To directly test whether CD4$^+$ T cells, CD8$^+$ T cells or both subsets were responsible for the eradication of UV2237m, mice were depleted of CD4$^+$ cells, CD8$^+$ cells, or both, by antibody treatments in vivo before H5IFN-β treatment (FIGS. 7-9). As expected, UV2237m tumors grew aggressively in mice depleted of CD4$^+$, CD8$^+$, or both, demonstrating that both subsets of T cells are necessary for eradication of UV2237m in intact mice (FIG. 10).

Example 6

Induction of Systemic Antitumor Activity by Intratumoral Injection of H5IFN-β Cells and Induction of Long-Term Specific Immunity To determine whether intratumoral injection of H5IFN-β to a UV2237m tumor at one site has a therapeutic effect on an untreated UV2237m tumor at distant site, mice were inoculated s.c. with $10^5$ UV2237m cells in the right flank and $10^5$ or $5\times10^3$ UV2237m cells in the left flank. On day 7–9, injection of H5mIFN-β into the right flank tumors of an average diameter of 5-mm resulted in complete regression of 100% (10 of 10) of both the tumor injected on the right flank and the left untreated tumors. In contrast, 0% (0 of 10) of the right treated or the left untreated tumors showed a complete regression in the group which the left flank tumors were established with $10^5$ cells (P<0.05), in the saline-treated groups, 0% (0 of 10) of the right treated or the left untreated tumors showed a complete regression in both groups which the left flank tumors were established with $5\times10^3$ or $10^5$ cells. These studies show that a systemic antitumor response is generated during treatment of a primary tumor, but the ability to successfully eradicated tumors at distant sites is inversely proportional to the tumor burden.

The following experiment was performed to assess whether intratumoral injection of H5IFN-β into an accessible s.c. tumor can also suppress distant pulmonary metastases. Mice bearing established s.c. UV2237 tumor (day 7 after $2\times10^5$ inoculation) were i.v. injected (via tail vein) with $4\times10^5$ UV2237m cells at day 7. Two days later H5IFN-β injected intravenously into the s.c. tumor resulted in the regression of all (10/10) of the s.c. tumors. Moreover, upon necropsy 28 days later, growth of lung metastases in those treated with intratumoral injection of H5IFN-β was abrogated as compared with that of control PBS based on visual observation and lung weights.

The results indicate that systemic antitumor activity induced by H5IFN-β is tumor specific.

Next, it was determined whether mice cured of their initial tumor by H5IFN-β develop long-term and specific immunity against the parental tumor. First, K1735m2 subcutaneous tumors, a weakly immunogenic melanoma, were eradicated by two weekly injections of H5IFN-β. K1735m2 melanomas were established by s.c. inoculation of $1.5\times1^{-5}$ cells, when the tumors reached 4–5-mm in diameter, they were given once or twice intratumoral injections of $2\times10^6$ lyophilized H5IFN-β at the interval of 1w. Complete eradication of tumors occurred in 80% of mice (8 of 10) receiving 2 injections of H5IFN-β. In mice receiving one injection of H5IFN-β, significant suppression tumor growth was noted, but not tumor regression. In a second set of experiments, the mice cured of their UV2237m tumors or K1735 m2 tumors were rechallenged by H5IFN-β, with $1.5\times10^5$ UV2237m or K1735m2 cells s.c., with $4\times10^5$ UV2237m or with $5\times10^4$ K1735m2 cells (mice rechallenged at least 45 days later after tumors regression, 10 mice/group) i.v. In 10/10 C3H mice cured of UV2237m tumors, the inventors observed no UV tumor growth s.c. or in the lung upon rechallenge but all mice challenged with K1735m2 s.c. had s.c. tumors or lung metastases respectively. In the mice cured of K1735m2 s.c. tumors by H5IFN-β, 100% of the mice rejected the K1735m2 s.c. or i.v. challenge but not s.c. or i.v. UV2237m, these results confirmed that the systemic antitumor immunity was tumor specific.

Example 7

Mechanisms

Figure 11:
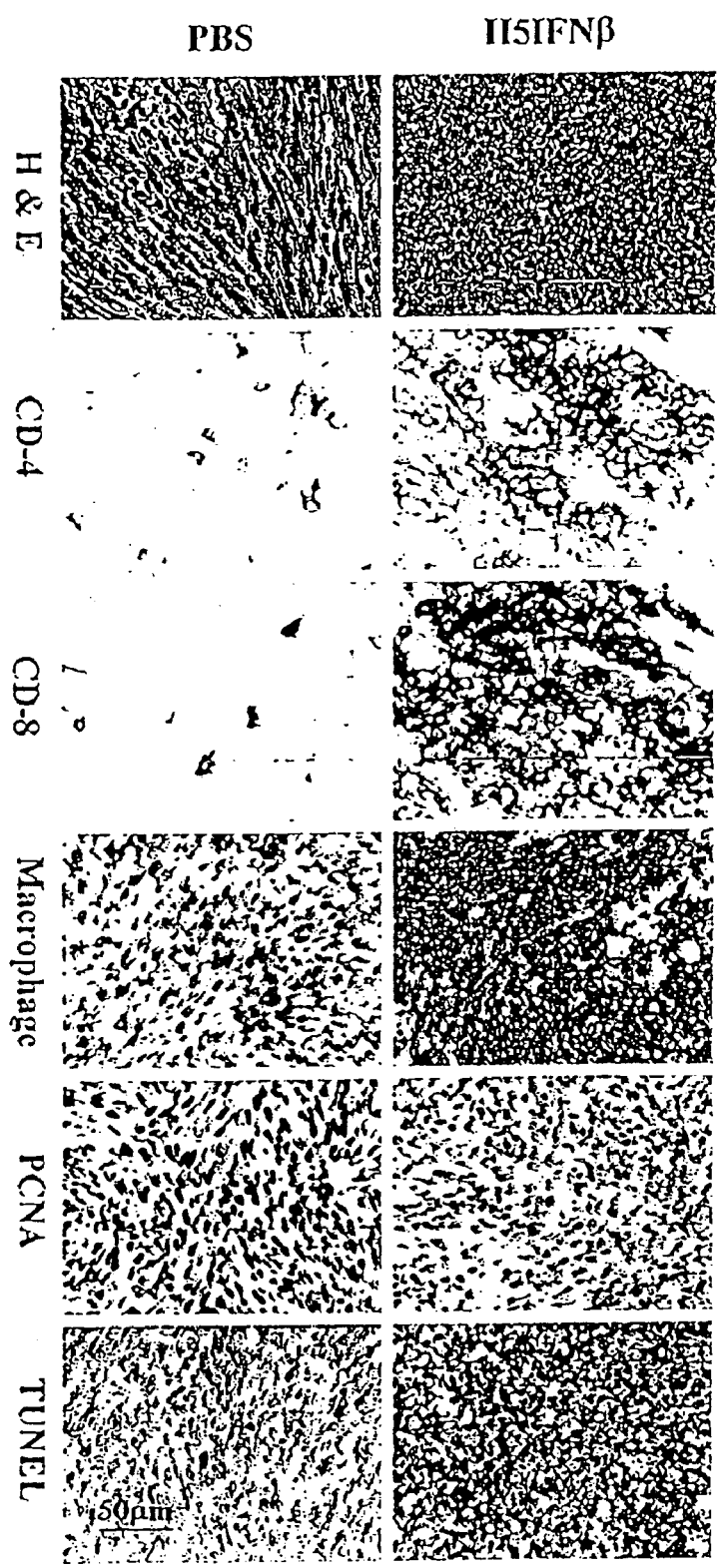
FIG. 11: Immunohistochemistry demonstrating tumor infiltration by immune cells.

To investigate the mechanisms underlying the eradication of UV2237m tumors, immunohistochemical staining for macrophages scavenger receptor, CD4$^+$-, CD8$^+$-T cells, or proliferating cell nuclear antigen (PCNA), and Terminal deoxynucleotidyl transferase-mediated dUTP-biotin nick-end labeling (TUNEL) were performed on frozen or paraffin sections of UV2237m tumors [U2237m tumors were established by s.c. inoculation of $2\times10^5$ UV2237m cells.] Immunohistochemical staining indicated that UV2237m tumors treated with H5IFN-β were densely infiltrated by macrophages and CD4$^+$ and CD8$^+$ T cells and contained significantly more cells stained positive by TUNEL method and much fewer PCNA-positive cells (FIG. 11).

Example 8

Figure 12:
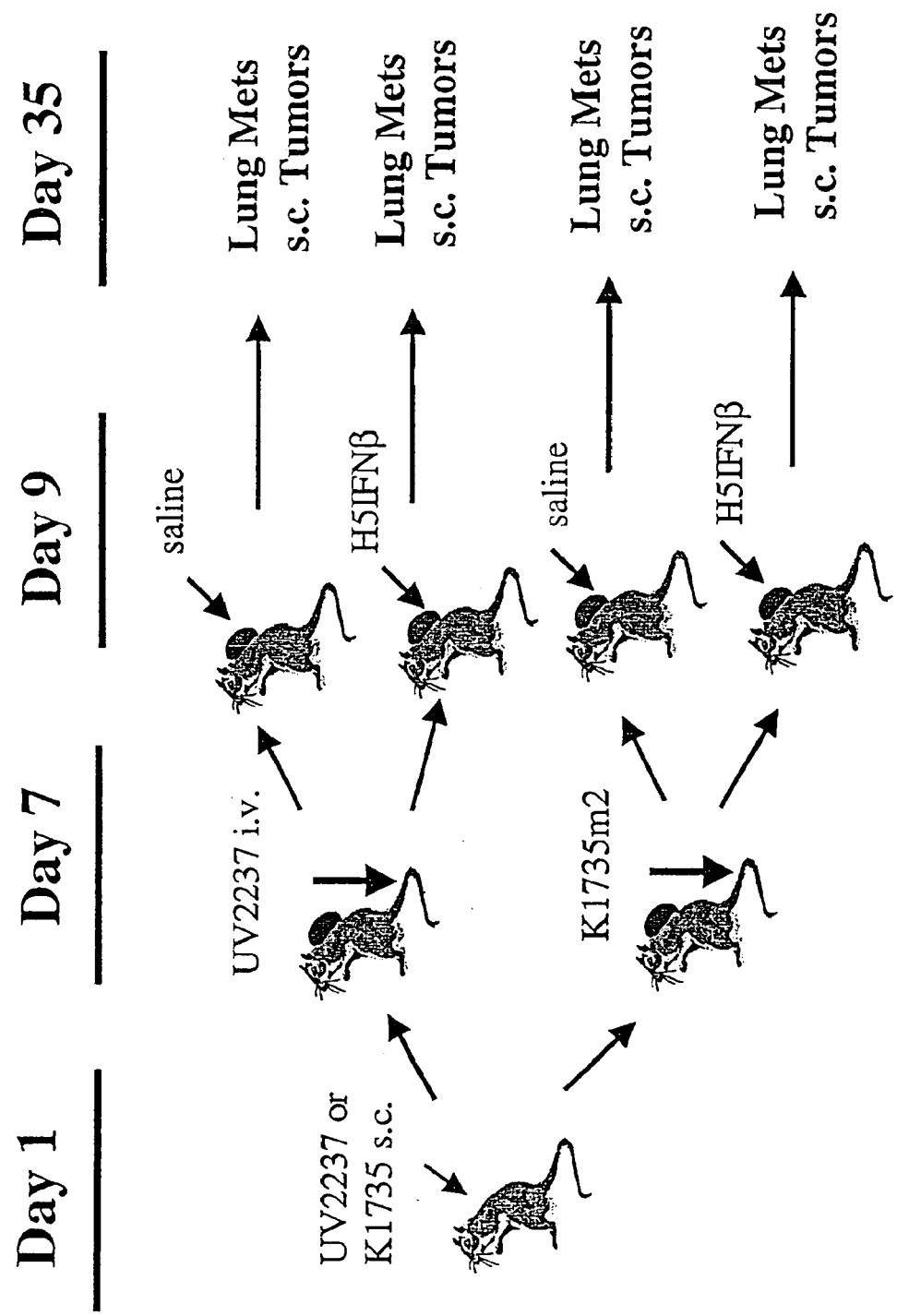
FIG. 12: Schematic description of systemic and tumor-specific immunity.

As set forth in FIG. 12, to investigate systemic and tumor specific immunity, UV2237m or K1735m2 cells were inoculated s.c. into C3H/HeN mice. When tumors were 4 mm in diameter (approximately day 7), the mice were injected i.v. with either UV2237m or K1735m2 cells. On day 9, the s.c. tumors were injected with either saline or lyophilized H5IFNβ at a concentration of $2\times10^6$ cells-equivalent. Injection was performed once for the UV2237 tumors and twice at 1 week intervals for K1735m2. The diameter of s.c. tumors was evaluated every 5 days. The mice were killed and the number of lung metastases counted 28 days after i.v. injection of the tumor cells.

As set forth in FIG. 13, UV2237 inoculated mice treated with H5IFNβ demonstrated marked regression of tumor growth in comparison with the saline control. A similar regression pattern was observed in K1735inoculated mice. The development of lung metastasis was also evaluated for each experimental group. Mice treated with H5IFNβ did not develop metastatic tissue. Conversely, mice treated with saline alone exhibited significant pulmonary metastasis.

Example 9

Mice with established s.c. UV2237m or K1735m2 tumors in C3H/HeN mice were cured by intratumoral injections of lyophilized H5IFNβ (one injection for UV2237m, two injections at 1 week intervals for K1735m2). Two months later, after the disappearance of the s.c. tumors, the cured mice were challenged either s.c. or iv. With either UV2237m or K1735m2 cells s.c. Tumor sizes were measured 2 weeks after inoculation. I.V. challenged mice were killed 4 weeks later. Their lungs were weighed and fixed in Bouin's solution. The lung tissue was examined for metastatic nodules under a dissecting microscope. As set forth in FIG. 14, mice treated and cured of UV2237m by treatment with H5IFNβ exhibited no metastatic growth when subsequently challenged with UV2237m cells. The response was determined to be tumor specific because challenge of UV2237 cured mice with inoculation of K1735 showed metastatic growth similar to that observed in controls. A similar tumor specific response was observed in mice cured of K1735m2 by H5IFNβ and subsequently challenged with either K1735m2 or UV2237.

Example 10

Materials and Methods

Reagents. Grace's medium, wild baculovirus, pBlue Bac His 2A baculovirus transfer vector, and liposome-mediated Bac-N-Blue Transfection Kit were purchased from Invitrogen Corporation (Carlsbad, Calif.). Eagle's minimum essential medium (EMEM), Ca2+- and Mg2+-free Hank's balanced salt solution (HBSS), and fetal bovine serum (FBS) were purchased from M. A. Bioproducts (Walkersville, Md.). EXCELL-400 medium was purchased from JRH Biosciences (Denver, Pa.).

Cells and Culture Condition. CT-26 murine colon carcinoma cells syngeneic to BALB/c mice were grown as monolayer cultures in MEM supplemented with 5% FBS, vitamins, sodium pyruvate, L-glutamine, and nonessential amino acids. The adherent monolayer cultures were incubated at 37° C. in humidified atmosphere containing 5% $CO_2$ in air. All cultures were free of mycoplasma, reovirus type 3, pneumonia virus of mice, K virus, encephalitis virus, lymphocyte choriomeningitis virus, ectromelia virus, and lactate dehydrogenase virus.

Insect cell lines Sf9 and the High Five (H5) were purchased from Invitrogen Corporation. Sf9 cells originated from the IPLBSF-21 cell line, derived from pupa of the fall army worm, Sopdoptera frugiperda. The H5 cell line originated from ovarian cells of the cabbage looper, Trichoplusia ni. The SF9 cells and the H5 cells were maintained as a monolayer culture in complete TNM-FH medium (Grace's medium supplemented with 10% FBS, Grace's medium supplements) and serum-free medium EXCELL 400, respectively, at 27° C. in non-humidified environment.

Preparation of Recombinant Baculoviruses. The full coding sequence of murine IFN-β cDNA (kindly provided by Dr. Taniguchi, Osaka University, Osaka, Japan) was subcloned into the baculovirus transfer vector pBlue Bac His2A to derive the recombinant vector pHis2AIFN-β. Recombinant baculovirus encoding IFN-β (BV-IFN-β) gene was produced by cotransfecting SF9 cells with pHis2AIFN-β and linearized Bac-N-Blue baculovirus DNA by using liposome-mediated Bac-N-Blue Transfection Kit (Invitrogen Corporation) and prepared in a large scale with the titer of $5\times10^8$ PFU/ml. H5 insect cells infected with BV-IFN-β (H5IFN-β) at 3 MOI for 48 h contained $2\times10^4$ units IFN-β, biological activity/$10^6$ cells (determined by Access Biomedical Research Laboratories, Inc, San Diego, Calif.).

Orthotopic Colon Cancer Animal Models. Specific pathogen-free male BALB/c mice were purchased from the Animal Production Area of the National Cancer Institute-Frederick Cancer Research Facility (Frederick, Md.). Animals were maintained according to institutional guidelines in facilities approved by the American Association of Laboratory Animal Care, in accordance with current regulations and standards of the United State Department of Agriculture, Department of Health and Human Services, and NIH. The mice were used according to institutional guidelines when they were 10 to 12 weeks old.

CT-26 colon cancer cells in exponential growth phase were harvested by a brief exposure to a 0.25% trypsin-0.1% EDTA solution. The cell suspension was pipetted to produce a single-cell suspension, washed, and resuspended in HBSS. Cell viability was determined by trypan blue exclusion, and only a single-cell suspension of greater than 90% viability was used. Mice anesthetized with intraperitoneum injections of Nembutal (30 mg/kg) were placed in the spine position. A lower midline abdominal incision was made and the cecum was exteriorized. Viable CT-26 cells ($5\times10^4$) were injected into the dome of the cecal wall (injection volume was 0.05 ml). A well-localized bleb was the sign of a technically satisfactory injection. The incision was closed in one layer with wound clips.

Figure 15:
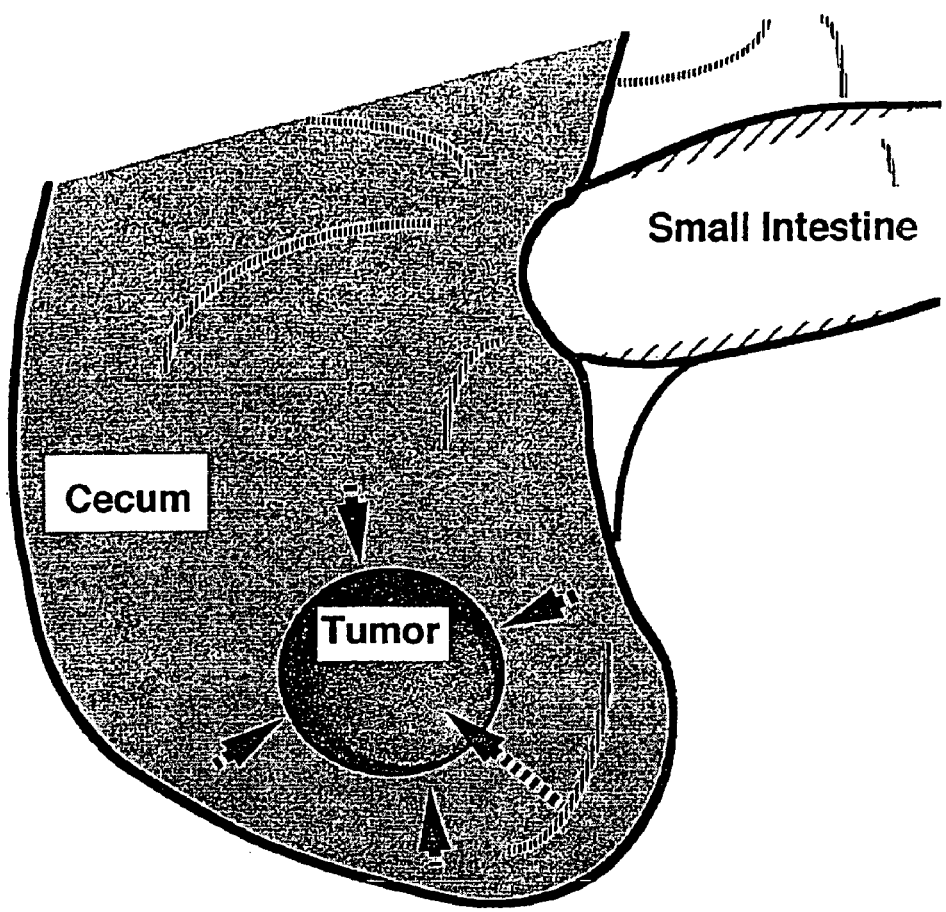
FIG. 15: Intratumoral injection of colon cancer: On day 0, groups of mice were injected with $1 \times 10^4$ viable CT-26 cells directly into the cecal wall. On day 14 or 21, all mice received laparotomy and 0.1 ml saline (control) with or without $2 \times 10^6$ H5 cells or H5 IFN-β cells were injected into the cecal tumor of cecum from serosa. Half of the volume was injected into the periphery of 4 areas of the tumor. The other half was injected directly into the center of the cecal tumor. Arrow shows the direction of injection.

Therapy with H5IFN-β. On days 14 and 21 after tumor implantation, the mice were anesthetized. Following laparotomy under Nembutal anesthesia, the cecal tumors were measured and 0.1 ml saline (for control), $2\times10^6$ H5 cells alone, or $2\times10^6$ H5 cells mIFN-β were injected into the cecal tumors (FIG. 15). The incision was closed in one layer with wound clips. The mice were killed when animals in the control group became moribund. Cecal tumor volume (TV) was estimated with the formula: TV=L (mm)×$W^2$ ($mm^2$)/2, where L and W represent the length and the width of the tumor mass, respectively. The percent of inhibition of cecal tumor growth was estimated with the formula: % inhibition= 1−(A/B)×100, where A and B represent the mean TV from control group mice and the mean TV from the group of mice treated with H5 cells or H5 mIFN-β cells, respectively.

The number of macroscopic spontaneous liver metastases was determined using a dissecting microscope after a 24-h fixation of the liver in Bouin's solution. When the number of metastases exceeded 100, the inventors assigned a value of >100. The number of liver lesions smaller than 1 mm in diameter was determined in representative tissue sections subsequent to Hematoxylin and Eosin staining using light microscopy.

Histology and Immunohistochemistry. Three primary cecal tumors from each groups were harvested at autopsy and divided into fragments which were placed in 10% (vol/vol) neutral formalin or OCT compound (Miles Laboratories, Elkhart, Ind.) to be snap-frozen in liquid nitrogen. For histological study, consecutive 5 μm sections were cut from each study block and stained with Hematoxylin and Eosin. For immunohistochemical analysis, frozen sections (10 μm) were fixed with cold acetone. Tissue sections (5 μm) of formalin-fixed, paraffin-embedded specimens were deparaffined in xylene, rehydrated in graded alcohol, and transferred to PBS for 12 min. Nonspecific reactions were blocked by incubating the section with a solution containing 5% normal serum and 1% normal goat serum for 20 min at room temperature. Excess blocking solution was drained and slides were incubated overnight at 4° C. with appropriate dilution (1:400) of monoclonal mouse anti-CD-31 antibody (Pharmingen, R&M), a 1:50 dilution of a mouse monoclonal anti-PCNA-PC10 antibody (Dako Co., Carpinteria, Calif.), a 1:200 dilution of mouse anti-CD4 antibody (American Type Culture Collection, R&M), a 1:200 dilution of mouse anti-CD8 antibody (Serotec, R&M), a 1:10 dilution of rat anti-mouse F4/80 (Rat Supranate), and a 1:200 dilution of rabbit polyclonal anti-iNOS (Transduction Laboratories, CITY, ST). The slides were rinsed with PBS three times and incubated with the appropriate dilution of secondary antibody conjugated anti-rabbit immunogloblin G (IgG) or anti rat IgG for 60 min. at room temperature. The slides were rinsed with PBS and color-developed by diaminobenzamin (Research Genetics, Huntsville, Ala.) for 5 min. The sections were then counterstained with Gill's Hematoxylin. A positive reaction in this assay stained reddish-brown in orecipitate in the cytoplasm.

Image Analysis to Quantify Intensity of Color Reaction for Expression of iNOS. Stained sections were examined in a Zeiss photomicroscope (Carl Zeiss, Inc., Thornwood, N.Y.) equipped with a three-chip-charged coupled device (CCD) color camera (model DXC-960 MD, Sony Corp., Tokyo, Japan). The images were analyzed using Optimas image analysis software (version 5.2, Bothell, Wash.). The slides were prescreened to determine the range in staining intensity of the slides to be analyzed. Images covering the range of staining intensities were captured electronically. A color bar (montage) was created and a threshold value was set in the red, green, and blue (RGB) modes of the color camera. All subsequent images were quantified based on this threshold. The integrated O.D. of the selected fields was determined based on its equivalence to the mean log inverse gray scale value multiplied by the area of the field. The samples were not counterstained, so the O.D. was due solely to the product of the immunoreaction. Five areas of 1 $mm^2$ at the center or edge of the tumor were measured from each slide. In each area, the O.D. for cytoplasmic staining of 10 tumor cells was measured. For image analysis, the intensity of staining for each factor was normalized by dividing the intensity of tumor cells in control group, which was set as 100.

Microvascular Density and Number of Effector Cells. Microvascular density and number of effector cells were measured at ten "hot spots" in the cecal tumor on CD31, CD4, CD8, and F4/80 antibodies stained specimens under 100-fold magnificent microscope fields. Areas containing the highest number of capillaries and small venules were identified by the tumor scanning the tumor sections at low power (×40). After the areas of high vascular density were identified, individual vessels were counted in ×100 fields (×10 objective and ×10 ocular, 0.14 $mm^2$ per field). The number of microvessels and effector cells were then adjusted to the number per 1 $mm^2$. On the basis of criteria for microvessel density described by Weidner et al., it was not necessary to observe a vessel lumen to classify a structure as a vessel.

TUNEL Method. Apoptotic cells in liver metastases were detected by the terminal deoxynucleotidyl transferase (TdT)-mediated dUTP-biotin nick and labeling (TUNEL), exactly as described previously.

Labeling Index. The labeling index for staining of PCNA, TUNEL method was determined by the percentage of the number of immunoreactive nuclei reactive to the total number of the nuclei examined. Three hot areas containing 100 nuclei each were examined and the average calculated.

CD31 and TUNEL Fluorescence Double Staining. Frozen cecal tumor tissue (8 $\mu$m thick) were fixed with cold acetone. The slides were rinsed three times by PBS and incubated with a protein block solution consisting of PBS (pH 7.5) containing 5% normal horse serum and 1% normal goat serum for 20 min at room temperature. Protein block solution was drained and slides were incubated overnight at 4° C. with the appropriate dilution (1:400) of monoclonal mouse anti-CD31 antibody (Pharmingen, R&M). The slides were removed from cold room to dark room, rinsed three times with PBS, and incubated with protein block solution for 10 min at room temperature. Slides were incubated with secondary antibody (Texas Red, Jackson, G&R, 1:200) and diluted in protein block solution for 1 h at room temperature. The samples were washed 6 times with PBS and added 4% paraformaldehyde in PBS for 10 min at room temperature. The samples were rinsed with PBS and incubated with 0.2% Triton X-100 in PBS for 15 min at room temperature. Slides were washed twice with PBS and added equilibration buffer from Apoptosis detection kit (Promega, 60 assays) for 10 min at room temperature. Excess equilibration buffer was removed and added incubation buffer (combining of 45 $\mu$l of equilibration buffer, 5 $\mu$l of nucleotide mix and 1 $\mu$l of TdT enzyme for each slide, Apoptosis detection kit) and incubated for 1 h at 37° C. The samples were incubated in 2×SSC in a coplin jar for 15 min at room temperature, washed with PBS three times, and nuclei were counterstained with Hoechst dye (Polysciences, INS. Warrington. Pa. #33342, 1:2000) for 10 min to identify total endothelial cells. The slides were mounted with glass cover slips and analyzed under a fluorescence microscope using a dual filter to view the green fluorescence of fluorescein at 520 nm and red fluorescence of Texas red at 600 nm. Total endothelial cells were identified by Hoechst stain filter. In this image analysis, endothelial cells revealed red color and TUNEL-positive cells revealed green color. It was thus determined that yellow color was apoptosis of endothelial cells (combination of red and green). Labeling index for apoptosis of endothelial cells method was determined by the percentage of the number of yellow points to the total number of endothelial cells in the periphery of tumor (10 areas in each tumor).

Statistical Analysis. The significance of the in vitro data was analyzed by the unpaired Student's t test. The significance of the in vivo data was analyzed by the Mann-Whitney U test. P values less than 0.05 were regarded as statistically significant.

Example 11

Results

Therapy of CT-26 Colon Cancer and Liver Metastasis. In the first set of studies, whether the intratumoral injection of H5 cells engineered to produce murine IFN-$\beta$ would inhibit tumorigenicity and liver metastasis was examined. Viable CT-26 cells ($5\times10^4$) were injected into the cecum of BALB/c mice. Two weeks after tumor implantation, the mice received a laparotomy and the cecal tumors were measured. All mice had cecal tumors of 5.7±0.3 mm (mean±SEM) at this time. Saline (control) (0.1 ml), or saline with $2\times10^6$ H5 cells or H5-mIFN-$\beta$ cells was injected into the cecal tumors. The mice became moribund, killed and necropsied 14 days after intratumoral injection (day 28 of the study). Cecal tumors and livers were removed. Primary cecal tumors were measured and liver metastases were counted for each group (n=10). While H5-mIFN-$\beta$ cell therapy tended to inhibit cecal tumor growth and liver metastasis, there was no significant difference between treatment group and control group (Table 2, Expt. 1)

TABLE 2

Treatment of cecal tumors and liver metastasis produced by CT-26 murine colon carcinoma by H5 IFN-$\beta$

| | | Liver metastasis | | |
|---|---|---|---|---|
| | | Metastasis no. | Cecal tumor | |
| Treatment | Incidence | Incidence Median (range) | Tumor volume ($mm^3$) | Inhibition (%) |
| Expt. 1 | | | | |
| Control | 7/9 | 9/9<br>11 (0–>100) | 1280 ± 364 | — |
| H5 | 6/7 | 6/7<br>12 (0–50) | 1417 ± 639 | −10 ± 49 |
| H5 IFN-$\beta$ | 5/9 | 9/9<br>2 (0–16) | 894 ± 240 | 30 ± 18 |
| Expt. 2 | | | | |
| Control | 6/8 | 8/8<br>5 (0–>100) | 859 ± 226 | — |

TABLE 2-continued

Treatment of cecal tumors and liver metastasis produced by CT-26 murine colon carcinoma by H5 IFN-β

| | Liver metastasis | | Cecal tumor | |
|---|---|---|---|---|
| | | Metastasis no. | | |
| Treatment | Incidence | Incidence Median (range) | Tumor volume (mm³) | Inhibition (%) |
| H5 | 5/8 | 8/8 3 (0−>100) | 580 ± 152 | 32 ± 17 |
| H5 IFN-β | 48 | 7/8 1 (0–14) | 202 ± 6[a] | 78 ± 7 |
| Expt. 3 | | | | |
| Control | 9/10 | 10/10 25 (0–95) | 1438 ± 290 | — |
| H5 | 9/10 | 10/10 6 (0–48) | 510 ± 79[b] | 64 ± 5 |
| H5 IFN-β | 4/9 | 8/9 0 (0–22)[a] | 266 ± 104[c] | 81 ± 7 |

Experiment 1. Groups of mice were implanted with 5 × 10⁴ viable CT26 cells directly in the cecal wall on day 0. On day 14, all mice received laparotomy and cecal tumors were measured. Saline (control) (0.1 ml), 2 × 10⁶ H5 cells, or H5 IFN-β cells were injected directly into the cecal tumor. All mice were killed on day 28 and cecal tumor volume and liver metastasis were evaluated. Tumor volume (TV) was calculated as follows: TV (mm³) = L (mm) × W² (mm²)/2, where L = length and W = width of the tumor. Inhibition (%) of TV was compared to the mean volume in the control group, assumed to be 0%. The value was the mean ± SEM. [a]P < 0.01; [b]P < 0.05; [c]P < 0.005 as compared with control. There was no significant inhibition of cecal tumor growth and liver metastasis in each group.
Experiment 2. Groups of mice were implanted with 1 × 10⁴ viable CT-26 cells directly in the cecal wall on day 0. On day 14, all mice received laparotomy and cecal tumors were measured. Saline (control) (0.1 ml), 2 × 10⁶ H5 cells, or H5 IFN-β cells were injected directly into the cecal tumor. All mice were killed on day 29 and the cecal tumor volume and liver metastasis were evaluated. H5 IFN-β therapy significantly inhibited cecal tumor growth.
Experiment 3. Groups of mice were implanted with 1 × 10⁴ viable CT-26 cells directly into the cecal wall on day 0. On days 14 and 21, all mice received laparotomy and cecal tumors were measured. Saline (control) (0.1 ml), 2 × 10⁶ H5 cells, or H5 IFN-β cells were injected directly into the cecal tumor. All mice were killed on day 31 and cecal tumor volume and liver metastasis were evaluated. H5 IFN-β therapy significantly inhibited cecal tumor growth and liver metastasis

TABLE 3

Expression of CD4, CD8, F4/80, and iNOS intensity of cytoplasm in the cecal tumor produced by CT-26 murine colon carcinoma with H5 IFN-β

| Treatment | CD4 (cells/mm²) | CD8 (cells/mm²) | iNOS intensity | F4/80 (cells/mm²) |
|---|---|---|---|---|
| Control | 115 ± 25 | 399 ± 44 | 100 ± 9 | 163 ± 36 |
| H5 | 141 ± 20 | 636 ± 66[a] | 127 ± 14 | 178 ± 35 |
| H5 IFN-β | 123 ± 19 | 825 ± 68[b,c] | 213 ± 14[c,d] | 397 ± 64[c] |

After tumor implantation, mice received two intratumoral injections of H5 IFN-β as described in footnote to Table 2, Expt. 3. All mice were killed and necropsied on day 31. Cecal tumors were harvested and processed for immunohistochemistry against antibodies of CD4, CD8, and F4/80. Each positive cell was counted at x100 field (0.14 mm²) in 10 areas of each slide. The numbers were then adjusted to the number of cells per 1 mm². For image analysis of iNOS, intensity of cytoplasm was evaluated by dividing the expression of intensity for control tumor cells assumed to be 100.
[a]P < 0.01; [b]P < 0.05; [c]P < 0.0001; [d]P < 0.0005 as compared with the group of mice treated with H5 cells. The value is the mean ± SEM. H5 IFN-β therapy induced CD8, F4/80, and iNOS expression in the lesion. Also see FIG. 5.

TABLE 4

Correlation of microvessel density with dividing and apoptotic tumor cells

| Treatment | Microvessel density (mm²) | PCNA⁺ tumor cells (%) | TUNEL⁺ tumor cells (%) |
|---|---|---|---|
| Control | 731 ± 35 | 86.7 ± 2.8 | 1.6 ± 0.2 |
| H5 | 295 ± 54[a] | 66.5 ± 7.7[b] | 5.8 ± 0.5[c] |
| H5 IFN-β | 198 ± 35[c] | 36.2 ± 4.0[c,d] | 14.0 ± 2.3[c,d] |

After tumor implantation, mice received intratumoral two injections of H5 IFN-β as described in footnote of Table 2, Expt. 3. Cecal tumors were harvested and processed for immunohistochemistry against antibodies for CD31, PCNA, and TUNEL assays. The percentages of dividing and apoptotic cells were counted as follows: dividing cells (%) = PCNA⁺ cells/100 nuclei × 100; apoptotic cells (%) = TUNEL⁺ cells/100 nuclei × 100.
[a]P < 0.0005; [b]P < 0.001; [c]P < 0.0001 as compared with control; [d]P < 0.005 as compared with the group of mice treated with H5. Value is mean ± SEM. H5 IFN-β therapy inhibited tumorigenicity and microvessel density in the lesion. Also see FIGS. 4 and 5.

In the second in vivo experiment, 1×10⁴ viable CT-26 cells were injected into the cecal wall of BALB/c mice. On day 14, the mice were anesthetized. Subsequent to laparotomy, cecal tumors were measured. All mice had tumors of 4.0±0.1 mm (mean±SEM). At this time, 0.1 ml saline (control) or 0.1 saline containing 2×10⁶ H5 cells or H5-mIFN-β cells was injected into the tumors. All mice were killed and necropsied 15 days after therapy (day 29 of the study). The results revealed a significant inhibition of cecal tumor growth in H5-IFN-β treatment group (reduced from 859±226 mm³ in control group to 202±69 mm³ in H5-mIFN-β treatment group, P<0.01). There was no significant inhibition for liver metastases in this treatment group compared with control group (Table 2, Expt. 2).

Figure 16:
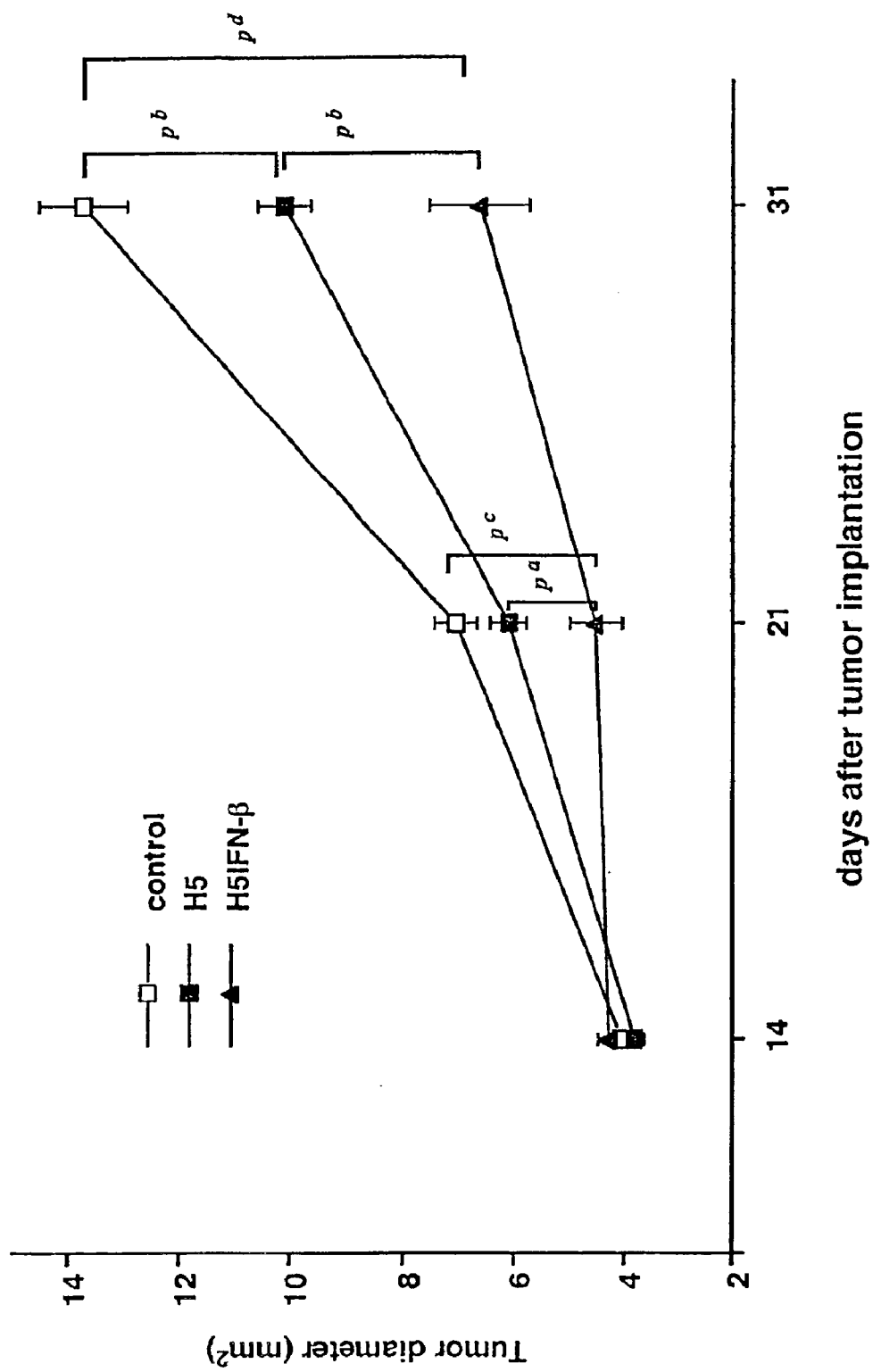
FIG. 16: Cecal tumor grown in treatment groups: After implantation of CT-26 colon cancer cells into the cecum, the mice received intratumoral injections of saline (control), H5 cells alone, or H5 IFN-β cells twice as described in FIG. 15. All mice were killed on day 31 and the cecal tumor was measured. $^a P<0.05$; $^b P<0.005$; $^c P<0.0005$; $^d P<0.0001$ as compared with the group of mice treated with saline or H5 cells alone. The value is mean±SEM.
Figure 17:
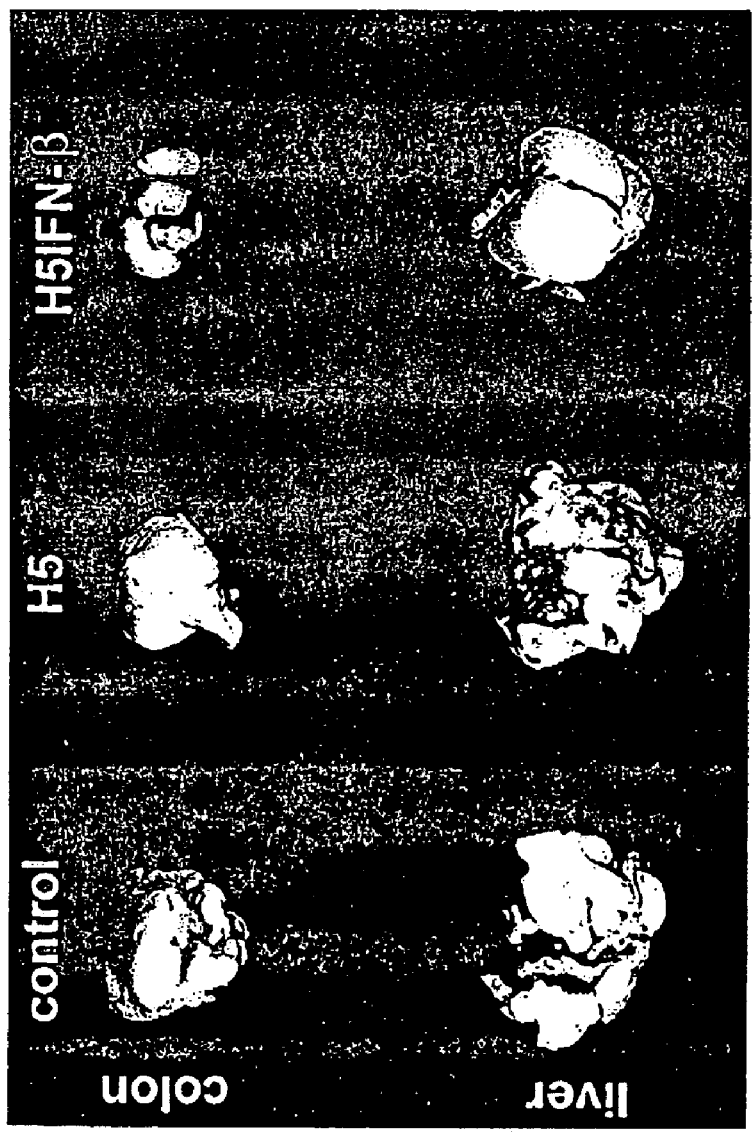
FIG. 17: Primary cecal tumor and liver metastases in treatment groups: After implantation of CT-26 cells into the cecum, the mice received intratumoral injections of saline (control), H5 cells alone, or H5 IFN-β cells as described in FIG. 15. All mice were killed and necropsied on day 31. Liver and cecum were harvested and cecal tumor size and the number of liver metastases were evaluated. Also see Table 2.

To determine whether multiple intratumoral injections of H5 mIFN-β cells would produce inhibitory effects, the inventors injected H5-mIFN-β cells into the cecal tumors twice. CT-26 (1×10⁴/inoculation) were injected into the cecal wall of BALB/c mice. Fourteen and 28 days after tumor cell implantation, the mice received laparotomy and cecal tumors were measured (FIG. 16). On day 14, all mice had cecal tumors of 4.0±0.1 mm (mean±SEM). After measuring the tumors, they were injected with 0.1 ml saline (control) or 0.1 ml saline containing 2×10⁶ H5 cells or H5-mIFN-β cells. Seven days after the last intratumoral injection, groups of mice received a laparotomy and the cecal tumors were measured again. At this time (day 21 of the study), the mice treated with H5 mIFN-β cells had a significant inhibition in colon tumor size as compared with control (4.51±0.47 mm versus 7.05±0.37 mm in diameter of control group, P<0.0005) or as compared with H5 alone (4.51±0.47 mm from 6.08±0.33 mm diameter of H5 alone, P<0.05). After measuring the tumor, intratumoral injection was repeated. Because some mice became moribund, all mice were killed and necropsied 10 days after the second intratumoral injection (day 31 of the study). Cecal tumors and livers were removed. Primary cecal tumors were measured and prepared for immunohistochemistry and the number of liver metastases was determined. The most significant inhibition for cecal tumor growth was found in H5 IFN-β treatment group (6.63±0.89 mm) as compared with the control group (13.73±0.79 mm, P<0.0001, or 266±104 as compared with 1438±290 mm³ tumor volume of control group), or H5 alone group (6.63±0.89 from 10.12±0.47 mm diameter of H5 alone group, p<0.005). Also, there was a significant inhibition for liver metastases between the control group and H5 IFNβ treatment group (P<0.01) (Table 2, Expt. 3; FIGS. 16 and 17).

Figure 18:
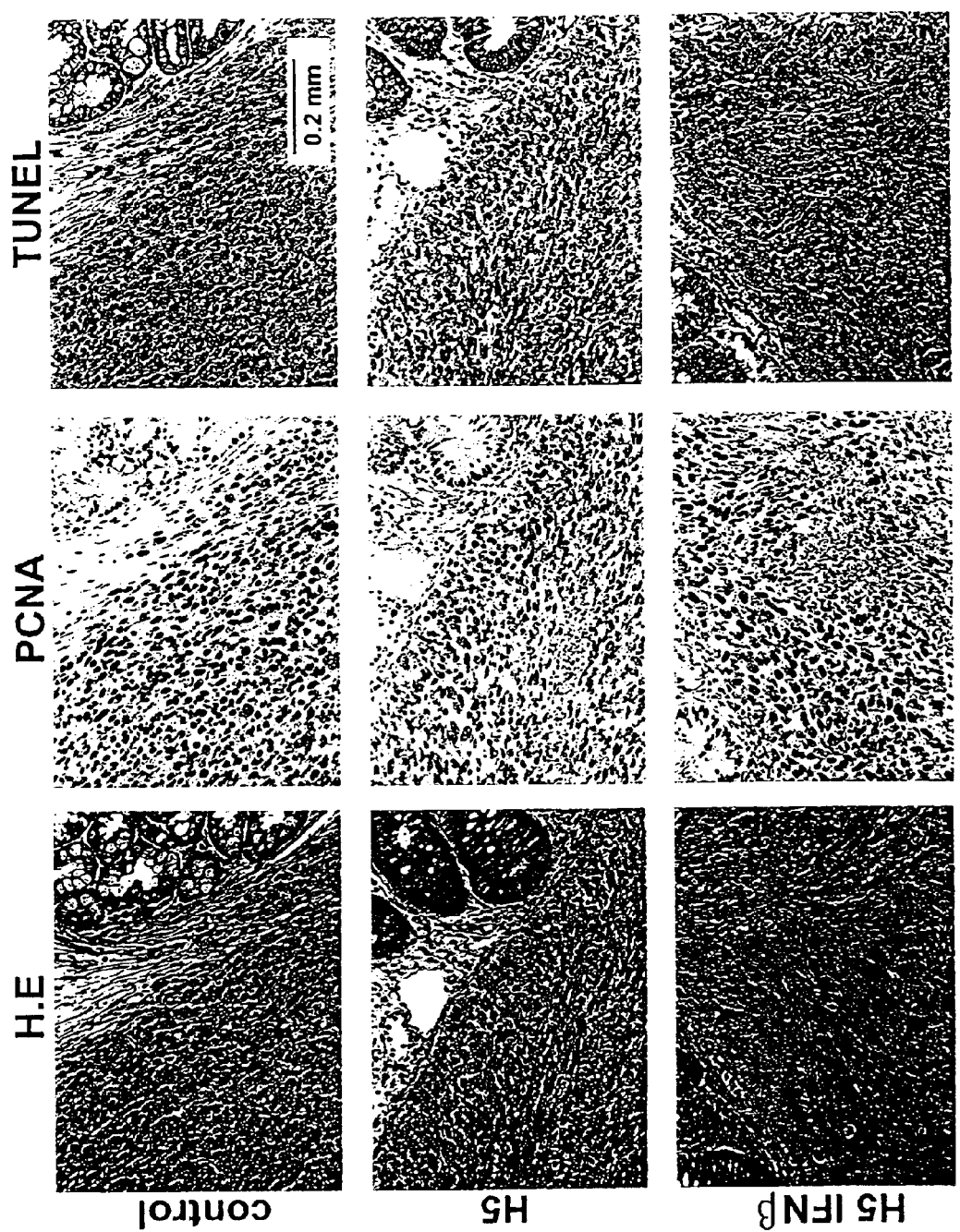
FIG. 18: Dividing cells and apoptotic cells in murine cecal tumors treated with H5 mIFN-β cells: After implantation of CT-26 cells into the cecum, intratumoral injection of H5 IFN-β were administrated twice as described in FIG. 15. Immunohistochemical analysis for PCNA and TUNEL assay revealed that high expression of dividing cells (PCNA+) and few apoptotic cells (TUNEL+) were observed in the cecal tumor of mice treated with saline. In sharp contrast, H5 IFN-β cell treatment revealed a decreased expression of dividing cells and an increase in apoptotic cells in the lesion. Also see Table 4.

Dividing Cells and Apoptotic Cells in Primary Colon Tumors. Immunohistochemical analysis for dividing cells and apoptotic cells (Table 4, FIG. 18) confirmed the results of inhibition for tumor growth by H5 IFN-β treatment. The percent of dividing cells (PCNA$^+$) in the primary cecal tumor was significantly reduced from a mean of 86.7±2.8% of tumors injected twice with saline (control) to 36.2±4.0% of tumors injected twice with H5 IFN-β cells (P<0.0001) or from a mean of 66.5±7.7% of mice treated with H5 cells (P<0.005). In sharp contrast, the percent of apoptotic cells in the lesions was significantly increased from a mean of 1.6±0.2% of tumors injected twice with saline (control) to 14.0±2.3% of tumors injected twice with H5 IFN-β cells (P<0.0001) or from a mean of 5.8±0.5% of tumors injected twice with H5 cells (P<0.005).

Figure 19:
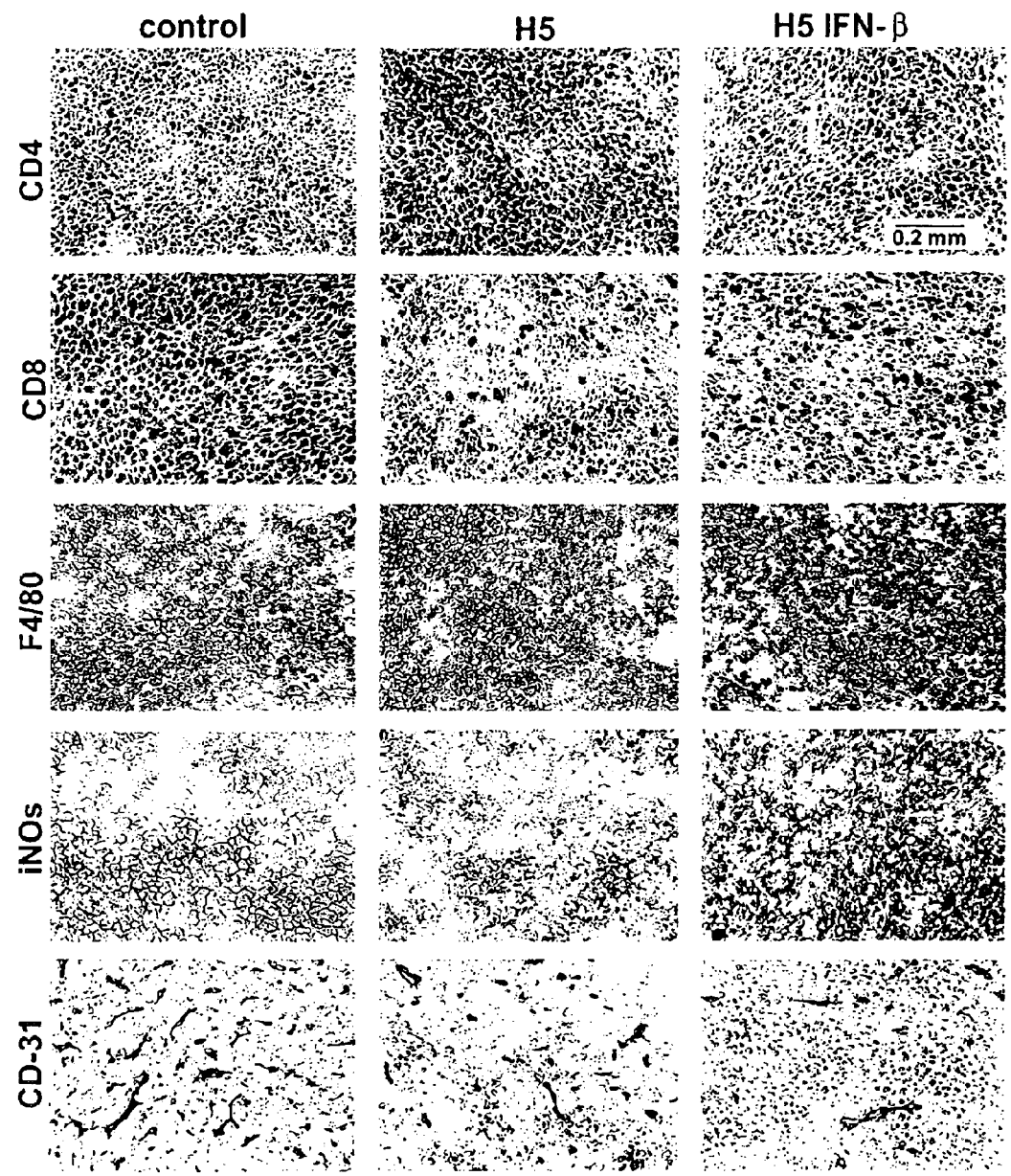
FIG. 19: Expression of CD4, CD8, F4/80, CD-31 and iNOS in the cecal tumor produced by CT-26 murine colon carcinoma following treatment with H5 IFN-β cells: After implantation of CT-26 cells into the cecum, intratumoral injection of H5 IFN-β was administrated twice as described in FIG. 16. Cecal tumors were harvested and processed for immunohistochemistry against antibodies of CD4, CD8, F4/80, CD31 and iNOS. An increased number of cytotoxic T-cells (CD8+), macrophages (F4/80), and high expression iNOS were observed in the lesions of mice treated with H5 IFN-β cells. In contrast, the number of endothelial cells (CD31+) were decreased in this treatment group. Also see Tables 3 and 4.

Microvessel Density in Primary Colon Tumors. To determine whether the therapeutic effect of intratumoral injection of H5 cells with IFN-β correlated with antiangiogenesis in the lesion, microvessel density was analyzed by immunohistochemical analysis for CD-31 antibody. The data show that the tumors treated with H5 IFN-β cells had significant inhibition for vascularization (198±35 vessels/mm$^2$ as compared with 731±35 vessels/mm$^2$ in the control tumors, P<0.0001) (Table 4, FIG. 19).

Expression of Effector Cells in the Primary Tumor. To determine whether the intratumoral injection of H5 IFN-β stimulated infiltration of effector cells, tissue sections were stained with antibodies against Helper T-cells (CD4), cytotoxic T cells (CD8), and macrophages (F4/80). Tumors injected with H5 IFN-β had high numbers of CD8$^+$ cells (825±69 mm$^2$ as compared to 399±44 mm$^2$ in control mice, P<0.0001, or 636±66 mm$^2$ in H5 cells alone, P<0.05) and macrophages (F4/80) (397±64 mm$^2$ as compared to 163±36 mm$^2$ in control mice, P<0.0001) (Table. 2, FIG. 19).

Intensity of iNOS in the Primary Tumor. Immunohistochemical analysis for iNOS confirmed stimulation of macrophages in the group of mice treated with H5 IFN-β (213±14 as compared to 100±9 in the tumor of mice treated with saline, P<0.0001, and 127±14 in the tumor of mice treated with H5 cells, P<0.0005) (Table 3, FIG. 19).

Figure 20:
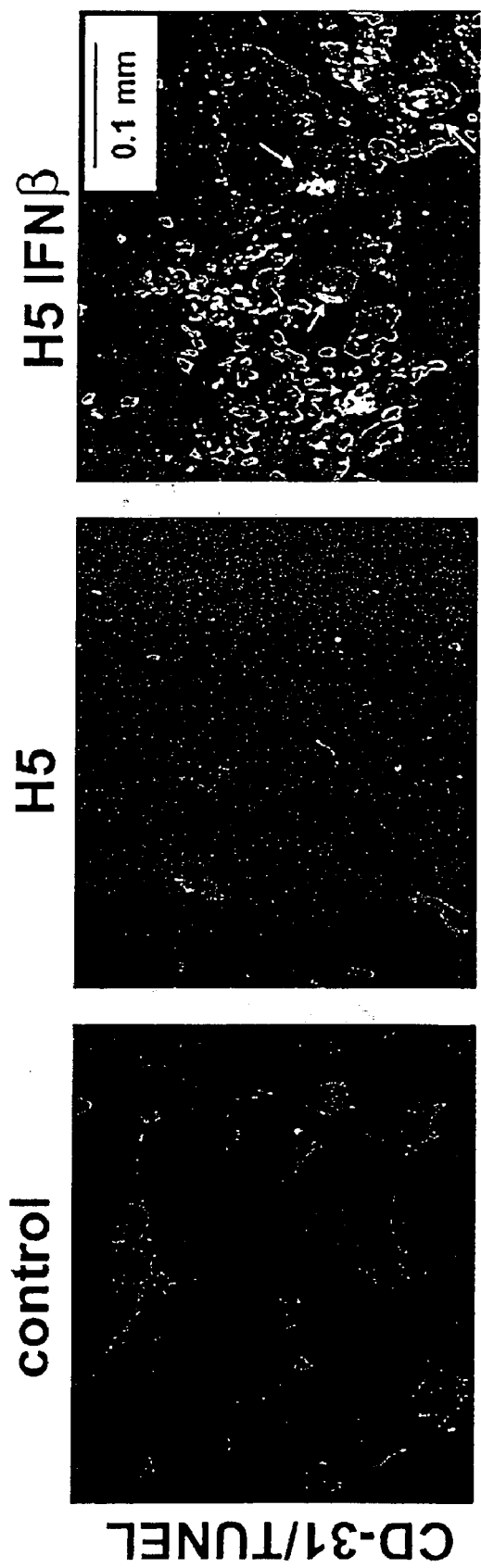
FIG. 20: Immunohistochemical double-staining against CD31 (endothelial cells) and TUNEL (apoptotic cells) in the cecal tumors treated with H5 IFN-β: Immunohistochemical double-staining against antibody for CD31 and TUNEL assay was performed for cecal tumor from each group. It was revealed that a number of CD31+ cells (red) and few TUNEL+ cells (green) were recognized in the lesion of mice treated with saline (control). In sharp contrast, a decreased number of CD31+ cells, increased number of TUNEL+ cells and endothelial cell apoptosis (arrow, yellow color) were recognized in the mice treated with H5 IFN-β cells.

H5 IFN-β-induced Apoptosis in Endothelial Cells in the Lesion. Immunohistochemical double staining for CD31 (red, to show endothelial cells) and TUNEL (green, to show apoptotic cells) demonstrated that tumors treated with H5 IFN-β had a high number of TUNEL$^+$ cells and a decreased number of endothelial cells (CD31). Intratumoral injections of H5 IFN-β cells induced endothelial cells to undergo apoptosis (yellow). There was no apoptosis in endothelial cells in the control groups (FIG. 20).

Example 12
Eradication of UV2337m by Sf9 or Sf21 Infected with Recombinant Baculovirus Encoding IFNβ Gene in C3H/HeN Mice Sf9 or Sf21 insect cells were infected with baculovirus encoding IFNβ at an MOI of 3. Mice were injected s.c. with 2×10$^5$ UV2237m cell equivalents per mouse. Seven days later, the mice were injected, intratumorally with either 100 μl PBS, 5×10$^6$ lyophilized Sf9IFNβ cells per tumor, 5×10$^6$ lyophilized Sf9IFNβ cells per tumor, 5×10$^6$ lyophilized Sf21BV cells per tumor or 5×10$^6$ lyophilized Sf21IFNβ cells per tumor. Tumor size was evaluated every five days.

Figure 21:
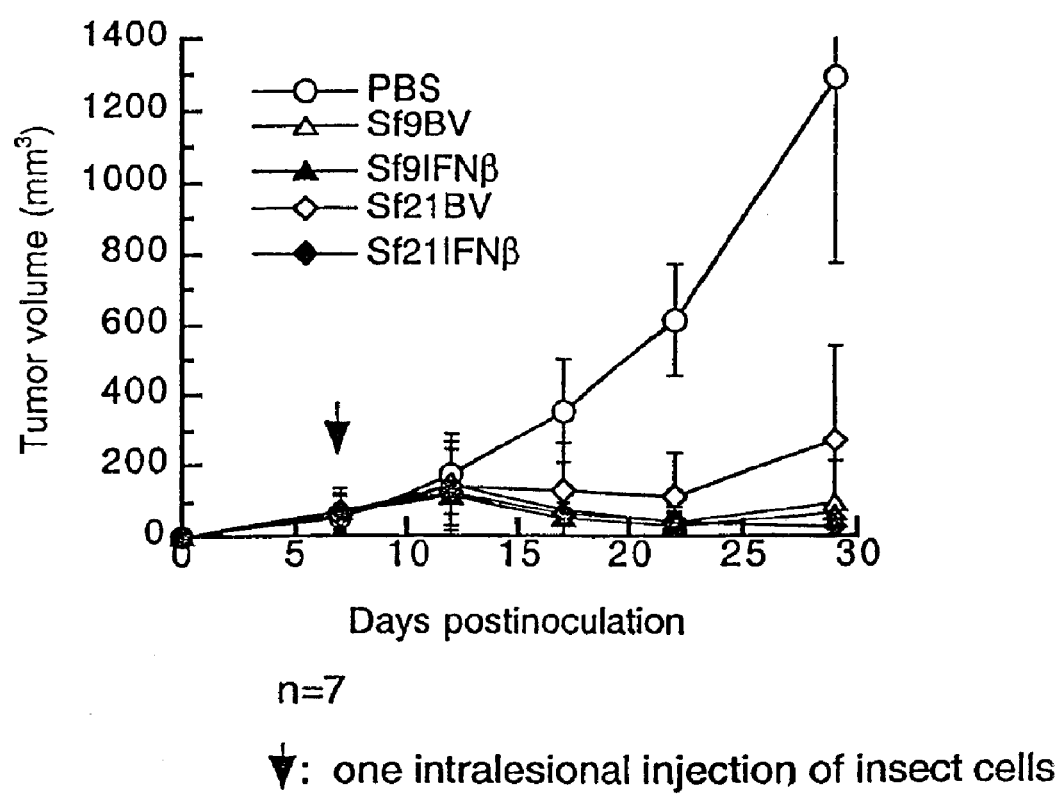
FIG. 21: Eradication of UV2237m fibrosarcomas by Sf9IFNβ and SfIFNβ.
Figure 22:
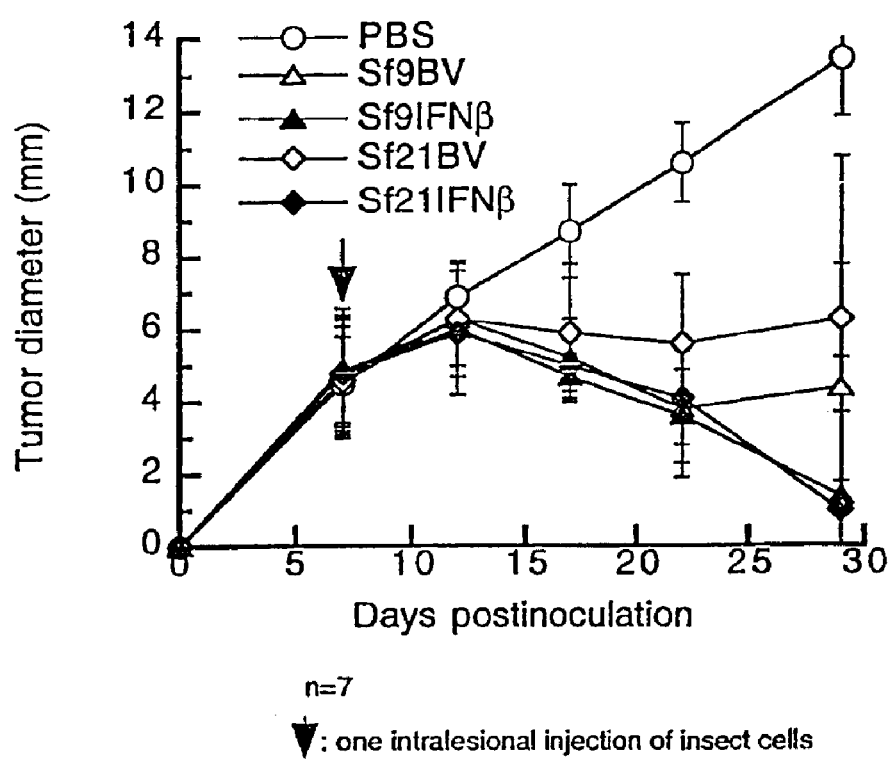
FIG. 22: Eradication of UV2237m fibrosarcomas by Sf9IFNβ and SfIFNβ.

As set forth in FIGS. 21 and 22, both Sf9IFNβ and Sf21IFNβ eradicated 6/7 of UV2237m fibrosarcomas. Sf9BV alone eradicated 2/7 tumors while SF21BV alone eradicated 1/7. This data demonstrates that cell types other than H5 function in the context of the instant invention.

Example 13

Figure 23:
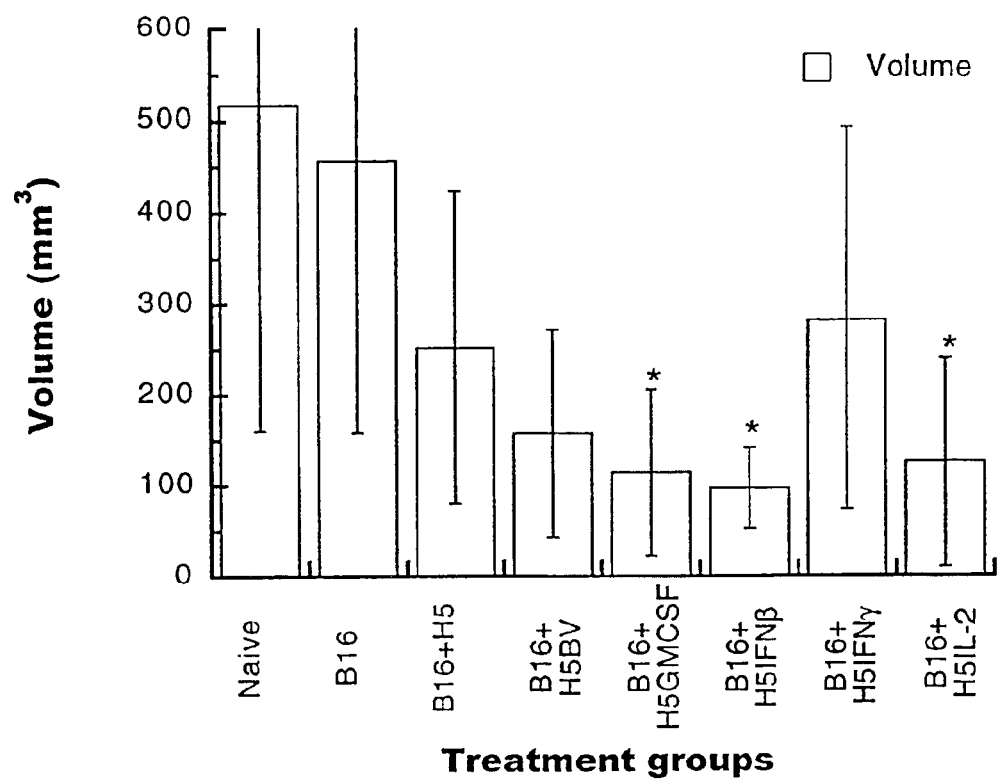
FIG. 23: Prophylaxis of B16BL6 melanoma growth in syngeneic C57BL/6 mice

Fifty C57BL6 mice were immunized twice at 2 weeks apart by s.c. inoculation of 2×10$^6$ irradiated B16BL6 tumor cells (a poorly immunogenic tumor) alone or mixed with 2×10$^6$ cell equivalents of one of the following: H %, H$_5$BV, H5IFNβ, H5IFNγ, H5IL-2 or H5GMCSF. Fourteen days after the second inoculation, the mice were challenged in the contralateral flank with viable 5×10$^4$ B16BL6 tumor cells. Naïve, age matched control mice were included. Melanoma size was measured 2 weeks after s.c. inoculation and tumor size evaluated by ANOVA. As set forth in FIG. 23, vaccination with a mixture of irradiated B16BL6 and lyophilized H5 cells infected with GM-CSF, IFNβ, or IL-2 resulted in a statistically significant reduction in challenge tumor growth.

Example 14

Figure 24:
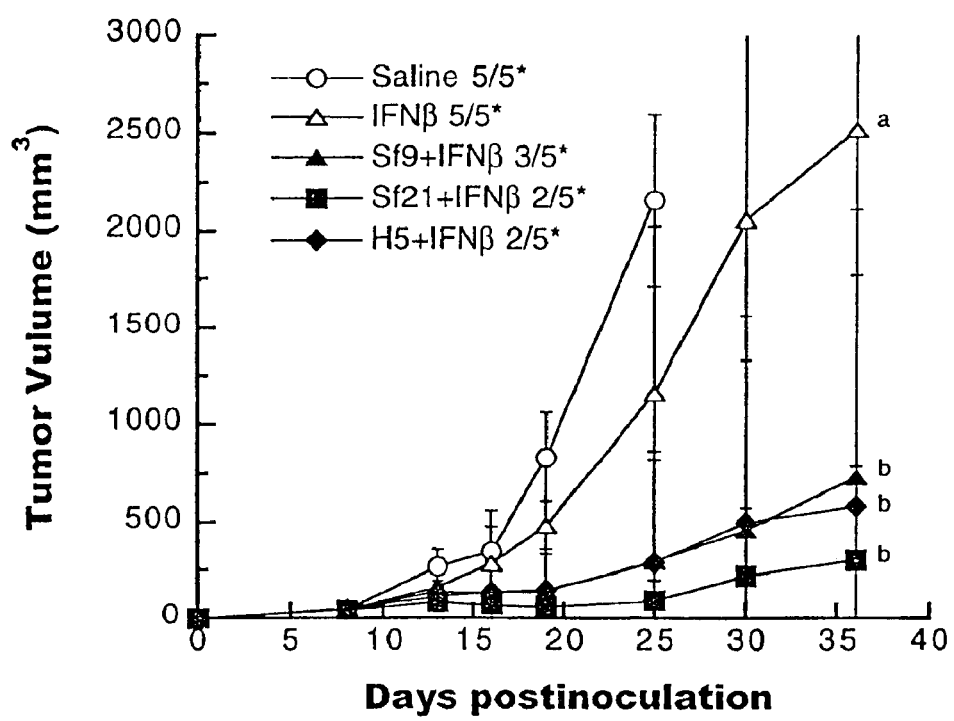
FIG. 24: Eradication of UV2237m fibrosarcomas by lyophilized insect cells with exogenous IPNβ.

Twenty mice were injected s.c with 2×10$^5$ UV2237 cells. Eight days later, the mice were given a single intratumoral injection of one of the following: saline, 10,000 U mIFNβ, 2×10$^6$ SF9 cell equivalents plus 10,000 U mIFNβ, 2×10$^6$ SF21 cell equivalents plus 10,000 U mIFNβ or 2×10$^6$ H5 cell equivalents plus 10,000 U mIFNβ. Tumor size was measured every 3–5 days and tumor size was evaluated by ANOVA. As set forth in FIG. 24, a significant difference in tumor volume was observed between mice injected with a combination of IFNβ and an insect cell composition and mice injected with either IFNβ alone or saline.

All of the compositions and methods disclosed and claimed herein can be made and executed without undue experimentation in light of the present disclosure. While the compositions and methods of this invention may have been described in particular terms, those of skill in the art appreciate that variations of these compositions, and in the steps or in the sequence of steps of the methods described herein, may be practiced without departing from the concept, spirit and scope of the invention. More specifically, it will be apparent that agents which are chemically and/or physiologically related may be substituted for the agents described herein while the same or similar results would be achieved.

H. REFERENCES

The following references, to the extent that they provide exemplary procedural or other details supplementary to those set forth herein, are specifically incorporated herein by reference.

Alt et al., *J. Biol. Chem.*, 253:1357–1320, 1978.
Ayres et al., *Virology* 202:586–605, 1994.
Bangham et al., *J. Mol. Biol.*, 13:238, 1965
Blissard and Rohrmann, *Virology* 170:537–555, 1989.
Blissard and Rohrmann, *Annu. Rev. Entomol.* 35:127–155, 1990.
Brutlag et al., *CABIOS*, 6:237–245, 1990.
Carson et al., *J. Virol.*, 65:945–951, 1991.
Chalfie et al., *Science*, 263:802–805, 1994.
Charlton and Volkman, *Virology*, 197, 245–254, 1993.
Chou and Fasman, *Biochemistry*, 13(2):211–222, 1974b.
Chou and Fasman, *Ann. Rev. Biochem.*, 47:251–276, 1978b.
Chou and Fasman, *Biophys. J*, 26:367–384, 1979.
Chou and Fasman, *Biochemistry*, 13(2):222–245, 1974a.
Chou and Fasman, *Adv. Enzymol. Relat. Areas Mol. Biol.*, 47:45–148, 1978a.
Colberre-Garapin et al., *J. Mol. Biol.*, 150:1–14, 1981.
Deamer and Uster, *LIPOSOMES*, M. Ostro ed., 1983.
Fetrow and Bryant, "*Biotech.*, 11:479–483, 1993.
Fidler, *Cancer Chemother. Pharmacol.* 43 Suppl:S3–10, 1999.
Geysen et al., *J. Immunol. Methods*, 102(2):259–74, 1987.
Geysen et al., *Proc Nat'l Acad Sci USA*, 81(13):3998–4002, 1984.
Ghosh and Bachhawat, "Targeting of liposomes to hepatocytes," In: Wu G. Wu C ed., Liver diseases, targeted diagnosis and therapy using specific receptors and ligands, New York: Marel Dekker, pp. 87–104, 1991.

Gregoriadis, *Drug Carriers In Biology And Medicine*, G. Gregoriadis (ed.), 1979, pp. 287–341.

Guarino and Summers, *J. Virol.*, 61:2091–2099, 1987.

Guarino et al., *J. Virol.*, 60:224–229, 1986.

Hooft van Iddekinge et al., *Virology*, 131:561–565, 1983.

Houghten, *Proc. Nat'l Acad. Sci. USA*, 82:5131–5135, 1985.

Jameson and Wolf, *Comput. Appl. Biosci.*, 4(1):181–186, 1988.

Kaneda et al., *Science*, 243:375–378, 1989.

Kato et al., *J. Biol. Chem.*, 266:3361–3364, 1991.

Kaufman, *Methods Enzymol.*, 185:537–566, 1990.

Kuzio et al., *Virology*, 139:414–418, 1984.

Martignoni et al., *J. Econ. Entomol.*, 75:1120–1124, 1982.

Nicolau et al., *Methods Enzymol.*, 149:157–176, 1987.

O'Reilly et al., *In: Baculovirus Expression Vectors*, W. H. Freeman and Company, N.Y, 1992.

Pardoll, *Immunol. Today*, 14:310–316, 1993.

"Remington's Pharmaceutical Sciences" 15th Edition, pages 1035–1038, 1570–1580, 1990.

Santerre et al., *Gene*, 30:147–156, 1984.

Sibille, et al., *J. Ex. Med.*, 172:35–45, 1990.

Summers and Smith, "A manual of methods for baculovirus vectors and insect cell culture procedures," *Tex. Agric. Exp. Stn. Bull.*, No.1555, 1987.

Szoka and Papahadjopoulos, *Proc. Nat'l Acad. Sci. U.S.A.* 75:4194–98, 1978.

Thiem and Miller, *J. Virol.*, 63:2008–2018, 1989.

U.S. Pat. No. 4,430,434.
U.S. Pat. No. 4,559,302.
U.S. Pat. No. 4,727,028.
U.S. Pat. No. 4,960,704.
U.S. Pat. No. 4,554,101.
U.S. Pat. No. 4,578,770.
U.S. Pat. No. 4,596,792.
U.S. Pat. No. 4,599,230.
U.S. Pat. No. 4,599,231.
U.S. Pat. No. 4,601,903.
U.S. Pat. No. 4,608,251.
U.S. Pat. No. 4,631,211.
U.S. Pat. No. 4,708,781.
U.S. Pat. No. 4,745,051.
U.S. Pat. No. 4,879,236.
U.S. Pat. No. 5,077,214.
U.S. Pat. No. 5,155,037.
U.S. Pat. No. 5,162,222.
U.S. Pat. No. 5,169,784.
U.S. Pat. No. 5,278,050.
U.S. Pat. No. 5,498,540.
U.S. Pat. No. 5,759,809.
U.S. Pat. No. 5,851,984.

Volkman et al., *Virology*, 148:288–297, 1986.

Weidner et al., *N. Engl. J. Med.* 324: 1–8. 1991.

Weinberger et al., *Science*, 228:740–742, 1985.

Whitford et al., *J. Virol.*, 63:1393–1399, 1989.

Wolf et al., *Comput. Appl. Biosci.*, 4(1):187–191, 1988.

What is claimed is:

1. A method of inhibiting cancer growth in a host having a cancer comprising:
    (a) isolating cancer cells from a said host;
    (b) rendering said cancer cells inactive;
    (c) reintroducing said inactivated cancer cells into said host in a pharmaceutical composition, said pharmaceutical composition further comprising an insect cell composition and interferon β.

2. The method of claim 1, wherein said cancer is localized.

3. The method of claim 1, wherein said cancer is metastatic.

4. The method of claim 1, wherein said insect cell composition comprises an exogenous DNA.

5. The method of claim 4, wherein said exogenous DNA is a baculovirus expression vector.

6. The method of claim 4, wherein said exogenous DNA encodes interferon β.

* * * * *